United States Patent
Bransby et al.

(10) Patent No.: US 11,021,683 B2
(45) Date of Patent: *Jun. 1, 2021

(54) TANGENTIAL FLOW DEPTH FILTRATION SYSTEMS AND METHODS OF FILTRATION USING SAME

(71) Applicant: REPLIGEN CORPORATION, Waltham, MA (US)

(72) Inventors: Michael Bransby, Altadena, CA (US); Derek Carroll, Los Angeles, CA (US)

(73) Assignee: Repligen Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/985,900

(22) Filed: Aug. 5, 2020

(65) Prior Publication Data

US 2020/0362290 A1  Nov. 19, 2020

Related U.S. Application Data

(63) Continuation of application No. 16/687,864, filed on Nov. 19, 2019, now Pat. No. 10,767,152, which is a continuation of application No. 16/297,263, filed on Mar. 8, 2019, now Pat. No. 10,538,727.

(60) Provisional application No. 62/640,175, filed on Mar. 8, 2018, provisional application No. 62/676,411, filed on May 25, 2018.

(51) Int. Cl.
*B01D 61/18* (2006.01)
*B01D 69/08* (2006.01)
*B01D 71/26* (2006.01)
*B01D 71/48* (2006.01)
*C12M 1/00* (2006.01)
*C12M 1/26* (2006.01)

(52) U.S. Cl.
CPC .............. *C12M 29/16* (2013.01); *B01D 61/18* (2013.01); *B01D 69/081* (2013.01); *B01D 71/26* (2013.01); *B01D 71/48* (2013.01); *C12M 29/10* (2013.01); *C12M 33/10* (2013.01); *B01D 2315/10* (2013.01); *B01D 2325/02* (2013.01)

(58) Field of Classification Search
CPC ........................... B01D 2325/02; C12M 29/16
See application file for complete search history.

(56) References Cited

U.S. PATENT DOCUMENTS

| | | |
|---|---|---|
| 3,095,343 A | 6/1963 | Berger |
| 2015/0125504 A1 | 5/2015 | Ward et al. |
| 2016/0199789 A1 | 7/2016 | Ebara et al. |
| 2017/0292103 A1 | 10/2017 | Cattaneo et al. |

OTHER PUBLICATIONS

Extended European Search Report dated Apr. 1, 2021 for corresponding European Patent Application No. 19764619.3.

*Primary Examiner* — Bradley R Spies
(74) *Attorney, Agent, or Firm* — Kacvinsky Daisak Bluni PLLC

(57) ABSTRACT

The present disclosure relates to hollow fiber tangential flow filters, including hollow fiber tangential flow depth filters, for various applications, including bioprocessing and pharmaceutical applications, systems employing such filters, and methods of filtration using the same.

29 Claims, 14 Drawing Sheets

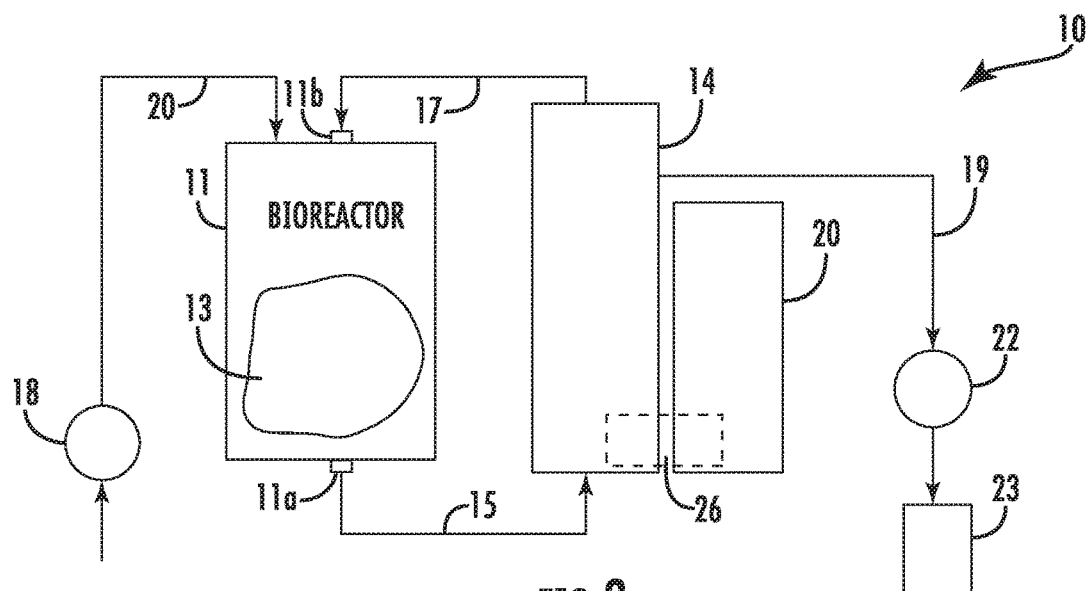
FIG. 3
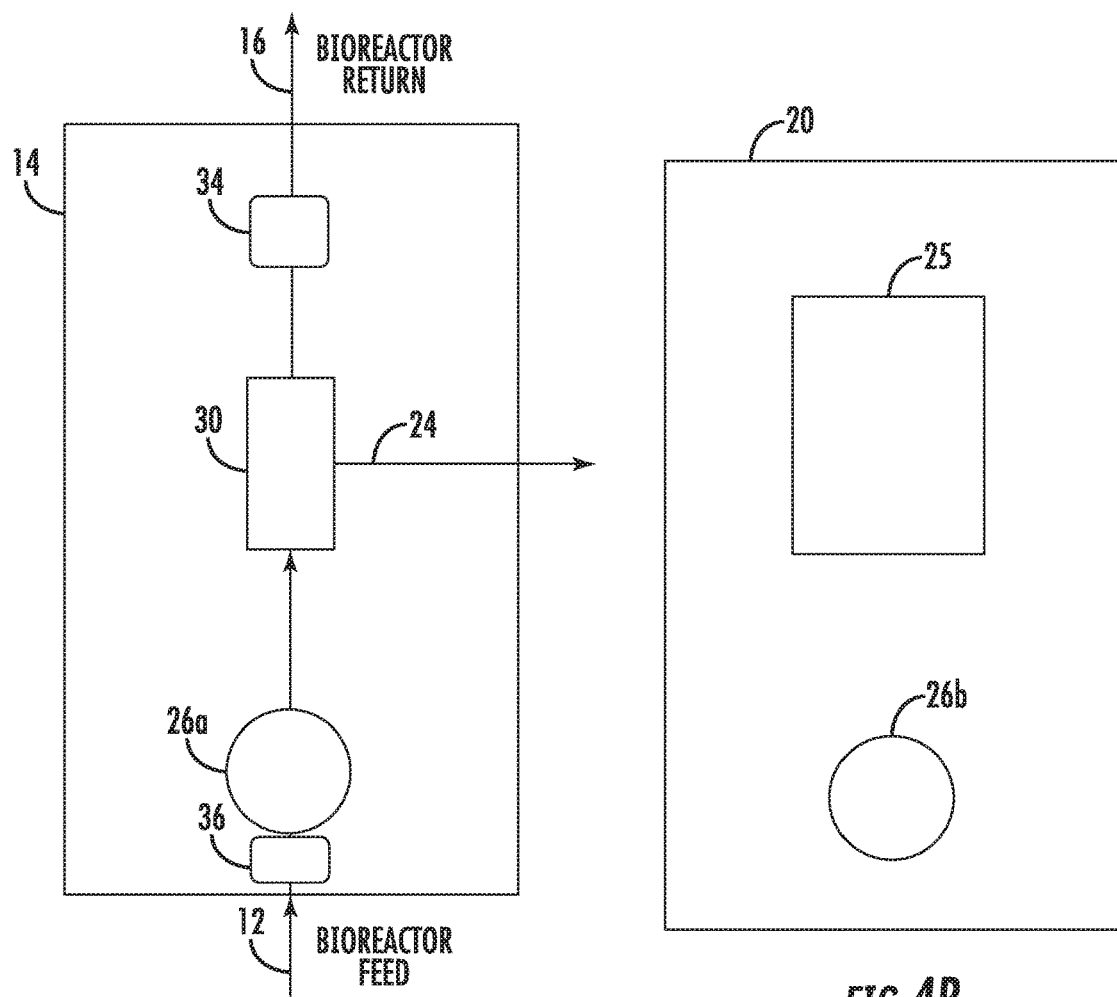
FIG. 4A
FIG. 4B

CONDITIONS SUMMARY

| CONDITIONS | [P3] |
|---|---|
| RECIRCULATION RATE; SHEAR RATE | MANUAL MODE (1900-2000 rpm) |
| MEDIA FEED RATE | MANUAL MEDIA FEED (TIMER CONTROLLED CYCLES) |
| PERMEATE RATE | CONTINUOUS MANUAL PERMEATION (CONSTANT PERMEATE rpm TO MATCH VVD) |
| PERFUSION CULTURE PERIOD (DAYS) | 9 (DAY 8-17) |
| FOULING EVENT | NONE EXPERIENCED |
| RUN END | PERMEATE LINE LEAK |

DATA SUMMARY

| | PERFUSION CULTURE PERIOD (DAYS) | PEAK VCD (10⁶ CELLS/ML) | PEAK %CELLS PASSING | TURBIDITY RANGE | | AVG %SIEVING | AVG TMP | FLUX RANGE (LMH) |
|---|---|---|---|---|---|---|---|---|
| | | | | RETENTATE | PERMEATE | | | |
| P3 | 9 | 175.0 | 4.79% | 1720-6250 | 354-1139 | 99.24 ± 14.85 | -- | 24-39 |

FIG. 7

TANGENTIAL FLOW DEPTH FILTRATION SYSTEMS AND METHODS OF FILTRATION USING SAME

PRIORITY

This application is a Continuation of, and claims the benefit of priority under 35 USC § 119 to U.S. Non-Provisional Patent application Ser. No. 16/687,864, filed Nov. 19, 2019 which is a Continuation of, and claims the benefit of priority under 35 USC § 119 to U.S. Non-Provisional Patent application Ser. No. 16/297,263, filed Mar. 8, 2019, and claims the benefit of priority under 35 USC § 119 to U.S. Provisional Patent application Ser. No. 62/640,175, filed Mar. 8, 2018, and to U.S. Provisional Patent Application Ser. No. 62/676,411, filed May 25, 2018, which is incorporated by reference herein in its entirety and for all purposes.

FIELD OF THE DISCLOSURE

Embodiments of this disclosure relate generally to process filtration systems, and more particularly to systems utilizing tangential flow depth filters.

BACKGROUND

Filtration is typically performed to separate, clarify, modify and/or concentrate a fluid solution, mixture or suspension. In the biotechnology and pharmaceutical industries, filtration is vital for the successful production, processing, and testing of new drugs, diagnostics and other biological products. For example, in the process of manufacturing biologicals, using animal or microbial cell culture, filtration is done for clarification, selective removal and concentration of certain constituents from the culture media or to modify the media prior to further processing. Filtration may also be used to enhance productivity by maintaining a culture in perfusion at high cell concentration.

Tangential flow filtration (also referred to as cross-flow filtration or TFF) systems are widely used in the separation of particulates suspended in a liquid phase, and have important bioprocessing applications. In contrast to dead-end filtration systems in which a single fluid feed is passed through a filter, tangential flow systems are characterized by fluid feeds that flow across a surface of the filter, resulting in the separation of the feed into two components: a permeate component which has passed through the filter and a retentate component which has not. Compared to dead-end systems, TFF systems are less prone to fouling. Fouling of TFF systems may be reduced further by alternating the direction of the fluid feed across the filtration element as is done in the XCell™ alternating tangential flow (ATF) technology commercialized by Repligen Corporation (Waltham, Mass.), by backwashing the permeate through the filter, and/or by periodic washing.

Modern TFF systems frequently utilize filters comprising one or more tubular filtration elements, such as hollow-fibers or tubular membranes. Where tubular filtration elements are used, they are typically packed together within a larger fluid vessel, and are placed in fluid communication with a feed at one end and at the other end with a vessel or fluid path for the retentate; the permeate flows through pores in the walls of the fibers into the spaces between the fibers and within the larger fluid vessel. Tubular filtration elements provide large and uniform surface areas relative to the feed volumes they can accommodate, and TFF systems utilizing these elements may be scaled easily from development to commercial scale. Despite their advantages, TFF systems filters may foul when filter flux limits are exceeded, and TFF systems have finite process capacities. Efforts to increase process capacities for TFF systems are complicated by the relationship between filter flux and fouling.

SUMMARY

The present disclosure relates to hollow fiber tangential flow filters, including hollow fiber tangential flow depth filters (also referred to as tangential flow depth filters), for various applications, including bioprocessing and pharmaceutical applications, systems employing such filters, and methods of filtration using the same.

In certain aspects, the present disclosure pertains to filtration of bioreactor fluids. Bioreactor systems provide an environment supporting biological activity, which results in the build-up of cell metabolites, including metabolic waste, in the bioreactor fluid. The buildup of metabolic waste limits cell amplification and/or cell growth within the bioreactor. As a result, known high capacity bioreactor systems require either a very large and expensive bioreactor or require filtering of bioreactor fluids to maintain optimal biological activity.

In various aspects, the present disclosure pertains to hollow fiber tangential flow filters, and in particular hollow fiber tangential flow depth filters, that comprise the following: a housing having an interior, a fluid inlet, a retentate fluid outlet, a permeate fluid outlet, and at least one hollow fiber comprising a porous wall, the at least one hollow fiber having an interior surface, an exterior surface, and a wall thickness ranging from 1 mm to 10 mm, from 2 mm to 7 mm, 1.5 mm to 2 mm, 2 mm to 5 mm, or the like, the interior surface forming an interior lumen having a width ranging from 0.75 mm to 13 mm, from 1 mm to 5 mm, 1 mm to 2 mm, or the like, and extending though the at least one hollow fiber. The at least one hollow fiber is positioned in the housing interior, the fluid inlet and the retentate fluid outlet are in fluid communication with the interior lumen of the at least one hollow fiber, and the permeate fluid outlet is in fluid communication with the housing interior and the exterior surface of the porous wall.

In some embodiments, the wall has a mean pore size ranging from 0.2 to 10 microns.

In some embodiments, which can be used in conjunction with the above aspects and embodiments, the at least one hollow fiber comprises a porous wall that is formed from a plurality of filaments that are bonded together.

In some embodiments, the filaments are extruded polymer filaments. For example, the extruded polymer filaments may be mono-component filaments. As another example, the extruded polymer filaments may be bi-component filaments. Bi-component filaments include those that contain a polyolefin and a polyester, for example, having a polyethylene terephthalate core and a polypropylene coating.

In some embodiments, which can be used in conjunction with the above aspects and embodiments, the extruded polymer filaments are melt-blown filaments.

In some embodiments, which can be used in conjunction with the above aspects and embodiments, a plurality of the extruded polymer filaments are bonded to one another at spaced apart points of contact to define the porous wall. For example, a plurality of the extruded polymer filaments may be thermally bonded to one another at spaced apart points of contact to define the porous wall, in which case the hollow fiber may be formed by assembling the extruded polymer filaments into a tubular shape and heating the extruded polymer filaments such that the extruded polymer filaments become bonded to one another, among other techniques.

In some embodiments, which can be used in conjunction with any of the above aspects and embodiments, the hollow fiber tangential flow filter comprises plurality of the hollow fibers. In these embodiments, the hollow fiber tangential flow filter may further comprising an inlet chamber positioned in an interior of the housing and in fluid communication with the fluid inlet, and an outlet chamber positioned in the interior of the housing and in fluid communication with the retentate fluid outlet, wherein the plurality of hollow fibers extend between the inlet chamber and the outlet chamber, and wherein the inlet chamber and the outlet chamber are in fluid communication with the interior lumen of each of the hollow fibers.

In various aspects, a hollow fiber tangential flow filter in accordance with any of the above aspects and embodiments, is used to separate a fluid that comprises large size particles and small size particles into a permeate comprising the small size particles and a retentate comprising the large size particles.

In various aspects, the present disclosure is directed to a filtration method that comprises introducing a fluid that comprises large size particles and small size particles into the fluid inlet of a hollow fiber tangential flow filter in accordance with any of the above aspects and embodiments, wherein the fluid is separated into a permeate comprising the small particles that exits the hollow fiber tangential flow filter through the permeate fluid outlet and a retentate comprising the large particles that exits the hollow fiber tangential flow filter through the retentate fluid outlet.

In some embodiments, which can be used in conjunction with the above aspects, the large particles may comprise cells, and the small particles may comprise one or more of proteins, viruses, virus like particles (VLPs), exosomes, lipids, DNA, and cell metabolites, among other possibilities.

In some embodiments, which can be used in conjunction with the above aspects, the fluid further comprises intermediate-sized particles that are trapped in the wall of the at least one hollow fiber. For example, the large particles may comprise cells, the intermediate-sized particles may comprise cell debris, and the small particles may comprise one or more of proteins, viruses, virus like particles (VLPs), exosomes, lipids, DNA, and cell metabolites, among other possibilities.

In some embodiments, which can be used in conjunction with the above aspects and embodiments, the large and small particles are of the same composition, and the method is used to separate the small particles from the large particles. For example, the large and small particles may be selected from ceramic particles, metal particles, liposomal structures for drug delivery, biodegradable polymeric particles, and microcapsules, among other possibilities.

In some embodiments, which can be used in conjunction with the above aspects and embodiments, the large particles, small particles and intermediate-sized particles are of the same composition and the method is used to separate the small particles from the large particles and to trap the intermediate-sized particles in the wall of the at least one hollow fiber. As above, the large, small particles and intermediate-sized particles may be selected from ceramic particles, metal particles, liposomal structures for drug delivery, biodegradable polymeric particles, and microcapsules, among other possibilities.

In various embodiments, which can be used in conjunction with any of the above aspects and embodiments, the fluid is fluid from a bioreactor and the retentate flow is circulated back into the bioreactor.

In various embodiments, which can be used in conjunction with any of the above aspects and embodiments, the fluid may be introduced into the fluid inlet in a pulsed flow. For example, the pulsed flow may be pulsed at a rate ranging from 1 cycle per minute to 1000 cycles per minute, among other possibilities.

In various aspects, the present disclosure is directed to tangential flow filtering systems that comprise a pumping system and a hollow fiber tangential flow filter in accordance with any of the above aspects and embodiments.

In various embodiments, the pumping system of the tangential flow filtering system is configured to deliver fluid to the fluid inlet of the hollow fiber tangential flow filter in a pulsed flow. For example, the pulsed flow may be pulsed at a rate ranging from 1 cycle per minute to 1000 cycles per minute, among other possibilities.

In various embodiments, which can be used in conjunction with the above aspects and embodiments, the pumping system of the hollow fiber tangential flow filtering system may comprise a pulsatile pump. For example, the pulsatile pump may be peristaltic pump.

In various embodiments, which can be used in conjunction with the above aspects and embodiments, the pumping system of the hollow fiber tangential flow filtering system may comprise a pump and a flow controller that causes the pump to provide the pulsed flow. For example, the flow controller may be positioned at the pump inlet or the pump outlet.

In some embodiments, the flow controller comprises an actuator that is configured to periodically restrict flow entering and/or exiting the pump thereby providing pulsed flow to the fluid inlet. For example, the actuator may be selected from an electrically controlled actuator, a pneumatically controlled actuator, or a hydraulically controlled actuator. For example, the flow controller may comprise a servo valve or a solenoid valve, among many other possibilities.

In various embodiments, which can be used in conjunction with the above aspects and embodiments, the pulsatile pump or flow controller of the tangential flow filtering system may be configured to provide a pulsed flow having a flow rate that is pulsed at a rate ranging from 1 cycle per minute to 1000 cycles per minute.

In various aspects, the present disclosure is directed to bioreactor systems that comprise (a) a bioreactor vessel configured to contain bioreactor fluid, the bioreactor vessel having a bioreactor outlet and a bioreactor inlet, (b) a hollow fiber tangential flow filtering system in accordance with any of the above aspects and embodiments, wherein the bioreactor outlet is in fluid communication with the fluid inlet and the bioreactor inlet is in fluid communication with the retentate outlet.

In various embodiments, the pumping system of the of the hollow fiber tangential flow filtering system is configured to provide pulsed flow of bioreactor fluid into the fluid inlet, thereby separating the pulsed flow of bioreactor fluid into a retentate flow which is re-circulated from the retentate outlet and into the bioreactor inlet and a permeate flow which is collected from the permeate fluid outlet either from the top or bottom of the housing. In certain embodiments, the pulsed flow may be pulsed at a rate ranging from 1 cycle per minute to 1000 cycles per minute, among other possibilities.

In various aspects, the present disclosure is directed to bioreactor systems comprising (a) a bioreactor vessel configured to contain bioreactor fluid, the bioreactor vessel having a bioreactor outlet and a bioreactor inlet, (b) a tangential flow filtering system comprising a pump and a hollow fiber tangential flow filter in accordance with any of the above aspects and embodiments, wherein the bioreactor outlet is in fluid communication with the fluid inlet and the bioreactor inlet is in fluid communication with the retentate outlet, and (c) a control system.

In various embodiments, the control system is configured to operate the pump such that a first flow of bioreactor fluid is pumped from the bioreactor outlet and into the fluid inlet, thereby separating the first flow of bioreactor fluid into a retentate flow which is re-circulated from the retentate outlet and into the bioreactor inlet and a permeate flow which is collected from the permeate fluid outlet.

In some embodiments, which can be used in conjunction with the above aspects and embodiments, the bioreactor system is configured to pump the first flow of bioreactor fluid in a pulsed fashion. For example, the pulsed flow may be pulsed at a rate ranging from 1 cycle per minute to 1000 cycles per minute, among other possibilities.

In various embodiments, a hollow fiber tangential flow filter for bioprocessing may include a housing having an interior, a fluid inlet, a retentate fluid outlet, and a permeate fluid outlet. At least one thick-walled hollow fiber may include a porous wall formed from at least one polymer. The thick-walled hollow fiber may have an average pore size and a density. The wall may define a lumen. The at least one hollow fiber may be disposed in the interior such that the fluid inlet and the retentate fluid outlet are in fluid communication with the lumen and the permeate fluid outlet is in fluid communication with the interior and the porous wall. The density may be between 51% and 56% of the density of an equivalent solid volume of the polymer filaments.

In various embodiments, the density may be about 53%. The average pore size may be about 2 μm with a 90% nominal retention. The polymer filaments may be melt-blown. The polymer filaments may be sintered. The polymer filaments may be selected from the group consisting of polyolefin, a polyester, and a combination thereof.

In various embodiments, A bioprocessing system may include a bioreactor. A tangential flow depth filtration (TFDF) unit may include a thick-walled hollow fiber formed from at least one polymer and may include a porous wall having a pore size and a density. The porous wall may define a lumen that is in fluid communication with the bioreactor. A permeate fluid outlet may be in fluid communication with the porous wall. A pump may be in fluid communication with the lumen. The density may be between 51% and 56% of the density of an equivalent solid volume of the polymer filaments.

In various embodiments, the average pore size may be about 2 μm with a 90% nominal retention. The density may be about 53%. The polymer filaments may be melt-blown. The polymer filaments may be sintered. The pump may be configured to provide a pulsed flow of fluid through the lumen.

In various embodiments, a method of culturing cells in a perfusion bioreactor system may include a culture vessel fluidly connected to a tangential flow depth filtration (TFDF) unit having a retentate channel and a filtrate channel. A culture medium may be flowed from the culture vessel through the retentate channel of the TFDF unit, whereby a fraction of the culture medium passes into the filtrate channel. A fluid may be returned from the retentate channel to the culture vessel. The culture medium may include at least 60×106 cells/mL. The method may be performed for at least 8 consecutive days. At least 80% of a plurality of cells of the culture medium may be viable throughout the 8 consecutive days. A volume of fresh culture medium may be added to the system that is equal to a permeate volume. Adding the volume of fresh culture medium may include adding at least 2 times a volume of the culture vessel to the system per day. The culture medium may include a bioproduct of interest. A rate of sieving of the bioproduct of interest may be at least 99% throughout the 8 consecutive days. The TFDF unit may include a thick-walled hollow fiber that may include melt-blown polymer filaments. A density of the thick-walled hollow fiber may be between 51% and 56% of the density of an equivalent solid volume of the polymer filaments. The density may be about 53%. The polymer filaments may be selected from the group consisting of polyolefin, a polyester, and a combination thereof.

In various embodiments, a method of processing a fluid comprising a bioproduct may include flowing a culture medium from a process vessel through a retentate channel of a TFDF unit. A fraction of the culture medium may pass into a filtrate channel. A fluid may be returned from the retentate channel to the process vessel. The filtrate channel may include a filter having a 2 mm internal diameter lumen therethrough. The filter may have an average pore size of about 2 μm. Flowing the culture medium may be performed at a shear rate of about 8000 s−1. The filter may have a flux above about 40 L·m−2·hr−1. The filter may have a flux of about 2300 L·m−2·hr−1. The flowing step may include the use of a pump selected from the group consisting of a centrifugal levitating magnetic pump, a positive displacement pump, a peristaltic, a membrane pump, and an ATF pump.

In various embodiments, a method of harvesting a bio material from a bioreactor system may include a process vessel fluidly connected to a tangential flow depth filtration (TFDF) unit having a feed/retentate channel and a filtrate channel. The method may include flowing a culture medium via a pump from the process vessel through the feed/retentate channel of the TFDF unit. A fraction of the culture medium may pass into the filtrate channel. The fluid may be returned from the feed/retentate channel to the process vessel. Fluid may be collected from the filtrate channel. The TFDF unit may include a thick-walled hollow fiber formed from at least one polymer and may include a porous wall. The thick-walled hollow fiber may have a density of about 53% of the density of an equivalent solid volume of the at least one polymer. The porous wall may define a lumen that is in fluid communication with the feed/retentate channel. The TFDF unit may have a flux above about 400 L·m−2·hr−1. The TFDF unit may have a peak cell passage of under 5%. The culture medium may include a bioproduct of interest. A rate of sieving of the bioproduct of interest may be at least 99%.

In various embodiments, the flowing step may include the use of a pump selected from the group consisting of a centrifugal levitating magnetic pump, a positive displacement pump, a peristaltic, a membrane pump, and an ATF pump.

In various embodiments, a method of harvesting a bio material from a bioreactor system may include a process vessel fluidly connected to a tangential flow depth filtration (TFDF) unit that may have a feed/retentate channel and a filtrate channel. A culture medium may be flowed via a pump from the process vessel through the feed/retentate channel of the TFDF unit. A fraction of the culture medium may pass into the filtrate channel. Fluid may be returned from the feed/retentate channel to the process vessel. Fluid may be collected from the filtrate channel. The TFDF unit may include a thick-walled hollow fiber formed from at least one polymer and may include a porous wall. The thick-walled hollow fiber may have a density of about 53% of the density of an equivalent solid volume of the at least one polymer. The porous wall may define a lumen that is in fluid communication with the feed/retentate channel. The TFDF unit may have a flux above about 400 L·m−2·hr−1. The TFDF unit may have a peak cell passage of under 5%. The culture medium may include a bioproduct of interest. A rate of sieving of the bioproduct of interest may be at least 99%.

In various embodiments, a method of harvesting a bio material from a bioreactor system may include a process vessel fluidly connected to a tangential flow depth filtration (TFDF) unit that may have a feed/retentate channel and a filtrate channel. A culture medium may be flowed through the feed/retentate channel of the TFDF unit. A fraction of the culture medium may pass into the filtrate channel. The fluid may be returned from the feed/retentate channel to the process vessel. The fluid may be collected from the filtrate channel. The TFDF unit may include a thick-walled hollow fiber formed from at least one polymer and may include a porous wall. The thick-walled hollow fiber may have a density of about 53% of the density of an equivalent solid volume of the at least one polymer. The porous wall may define a lumen that is in fluid communication with the feed/retentate channel.

In various embodiments, a pore size of the porous wall may be about 2 μm with a 90% nominal retention. The flowing step may include the use of a pump selected from the group consisting of a centrifugal levitating magnetic pump, a positive displacement pump, a peristaltic, a membrane pump, and an ATF pump.

BRIEF DESCRIPTION THE DRAWINGS

The above and other aspects of the present disclosure will be more apparent from the following detailed description, presented in conjunction with the following drawings wherein:

FIG. 3 is a schematic illustration of a bioreactor system according to the present disclosure.

FIG. 4A is a schematic illustration of a disposable portion of a tangential flow filtering system according to the present disclosure.

FIG. 4B is a schematic illustration of a reusable control system according to the present disclosure.

FIG. 7 shows various metrics of a filter of FIG. 6.

DETAILED DESCRIPTION

Overview

The embodiments of this disclosure relate, generally, to TFDF, and in some cases to TFDF systems and methods for use in bioprocessing, particularly in perfusion culture and harvest. One exemplary bioprocessing arrangement compatible with the embodiments of this disclosure includes a process vessel, such as a vessel for culturing cells (e.g., a bioreactor) that produce a desired biological product. This process vessel is fluidly coupled to a TFDF filter housing into which a TFDF filter element is positioned, dividing the housing into at least a first feed/retentate channel and a second permeate or filtrate channel. Fluid flows from the process vessel into the TFDF filter housing are typically driven by a pump, e.g., a mag-lev, peristaltic or diaphragm/piston pump, which may impel fluid in a single direction or may cyclically alternate the direction of flow.

Bioprocessing systems designed to harvest a biological product at the conclusion of a cell culture period generally utilize a large-scale separation device such as a depth filter or a centrifuge in order to remove cultured cells from a fluid (e.g., a culture medium) containing the desired biological product. These large scale devices are chosen in order to capture large quantities of particulate material, including aggregated cells, cellular debris, etc. However, the trend in recent years has been to utilize disposable or single-use equipment in bioprocessing suites to reduce the risks of contamination or damage that that accompanies sterilization of equipment between operations, and the costs of replacing large scale separation devices after each use would be prohibitive.

Additionally, industry trends indicate that bioprocessing operations are being extended or even made continuous. Such operations may extend into days, weeks, or months of operation. Many typical components, such as filters, are unable to adequately perform for such lengths of time without fouling or otherwise needing maintenance or replacement.

Additionally, in bioprocessing it is often desirable to increase process yields by increasing cell density. However, increasing cell density in may be complicated by increased filter fouling, etc.

Embodiments of this disclosure address these challenges by providing economical filtration means that are tolerant of increased cell densities, extended process times, and suitable for use in harvest. The inventors have discovered that tangential flow depth filters made by melt blowing of polymers or polymer blends can be manufactured at a comparatively low-cost compatible with single use, yet are able to operate for extended periods, at high fluxes, and at increased cell densities.

Exemplary Embodiments

Figure 1A:
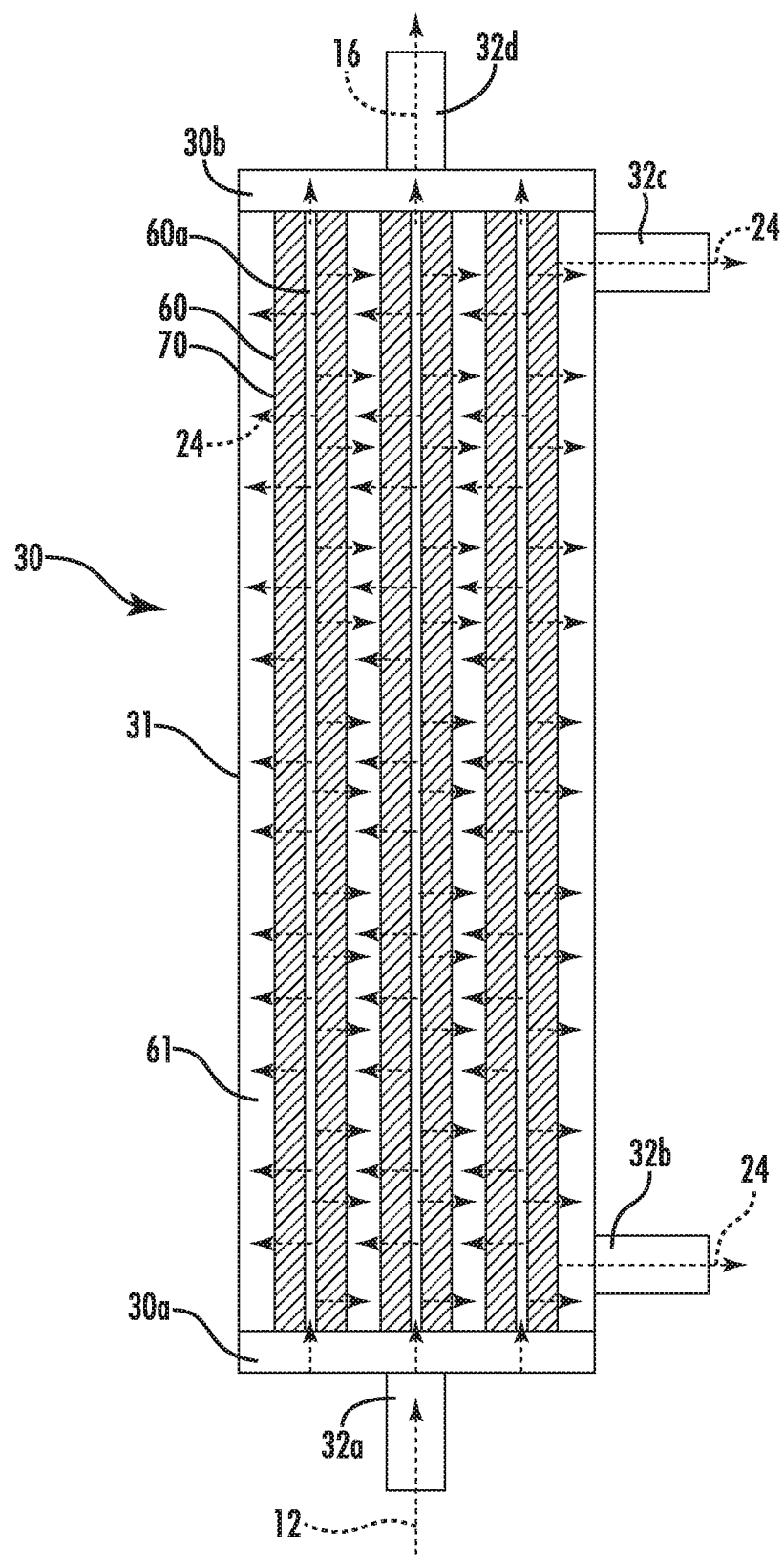
FIG. 1A is a schematic cross-sectional view of a hollow fiber tangential flow depth filter according to the present disclosure.

A schematic cross-sectional view of a hollow fiber tangential flow filter 30 in accordance with present disclosure is shown in FIG. 1A. The hollow fiber tangential flow filter 30 includes parallel hollow fibers 60 extending between an inlet chamber 30a and an outlet chamber 30b. A fluid inlet port 32a provides a flow 12 to the inlet chamber 30a and a retentate fluid outlet port 32d receives a retentate flow 16 from the outlet chamber 30b. The hollow fibers 60 receive the flow 12 through the inlet chamber 30a. The flow 12 is introduced into a hollow fiber interior 60a of each of the hollow fibers 60, and a permeate flow 24 passes through walls 70 of the hollow fibers 60 into a permeate chamber 61 within a filter housing 31. The permeate flow 24 travels to permeate fluid outlet ports 32b and 32c. Although two permeate fluid outlet ports 32b and 32c are employed to remove permeate flow 24 in FIG. 1A, in other embodiments, only a single permeate fluid outlet port may be employed. Filtered retentate flow 16 moves from the hollow fibers 60 into the outlet chamber 30b and is released from the hollow fiber tangential flow filter 30 through retentate fluid outlet port 32d.

Figure 1B:
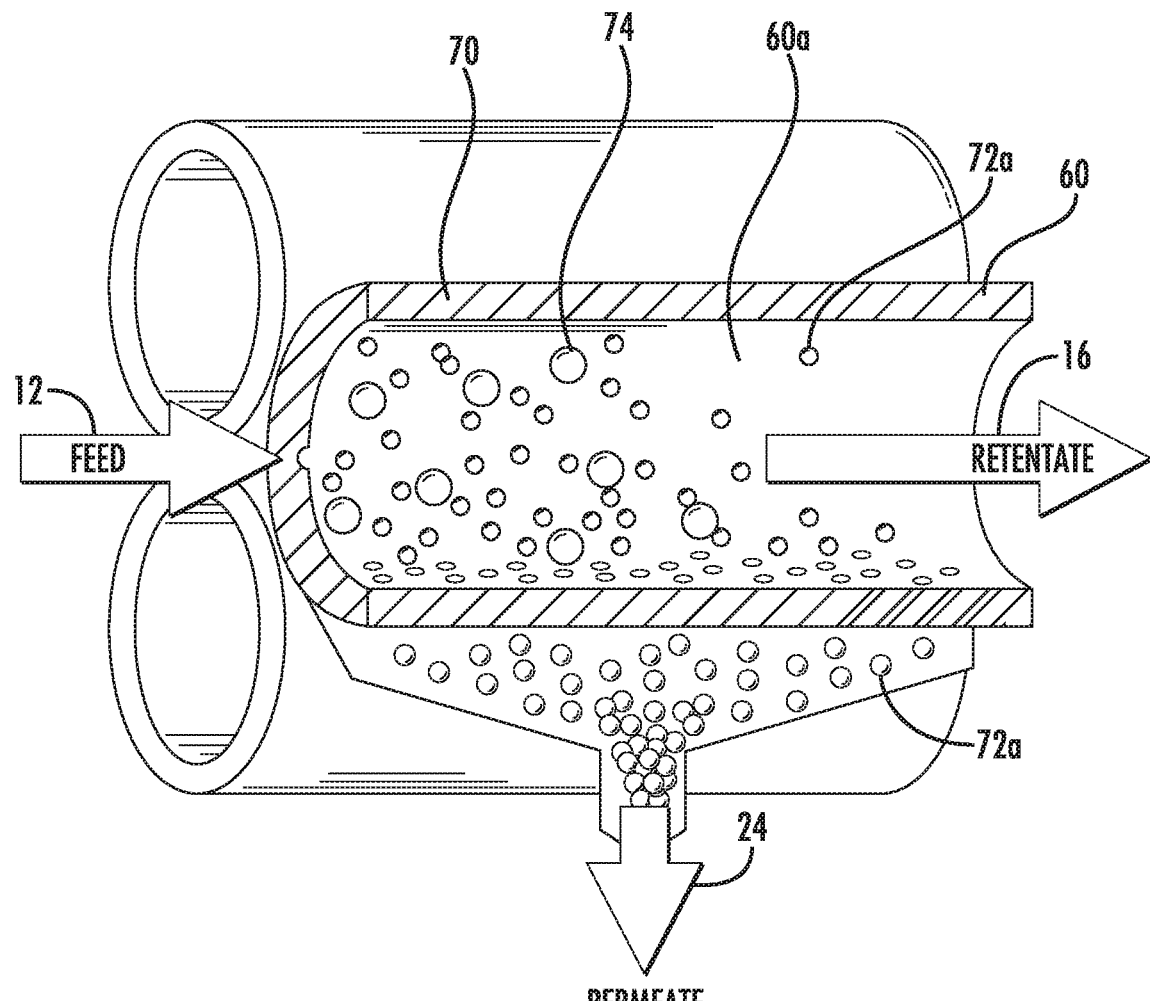
FIG. 1B is a schematic partial cross-sectional view of three hollow fibers within a tangential flow filter like that shown in FIG. 1A.

FIG. 1B is a schematic partial cross-sectional view of three hollow fibers 60 within a hollow fiber tangential flow filter analogous to that shown in FIG. 1A, and shows the separation of an inlet flow 12 (also referred to as a feed) which contains large particles 74 and small particles 72a into a permeate flow 24 containing a portion of the small particles and a retentate flow 16 containing the large particles 74 and a portion of the small particles 72a that does not pass through the walls 70 of the follow fibers 60.

Tangential flow filters in accordance with the present disclosure include tangential flow filters having pore sizes and depths that are suitable for excluding large particles (e.g., cells, micro-carriers, or other large particles), trapping intermediate-sized particles (e.g., cell debris, or other intermediate-sized particles), and allowing small particles (e.g., soluble and insoluble cell metabolites and other products produced by cells including expressed proteins, viruses, virus like particles (VLPs), exosomes, lipids, DNA, or other small particles). As used herein a "microcarrier" is a particulate support allowing for the growth of adherent cells in bioreactors.

Figure 2:
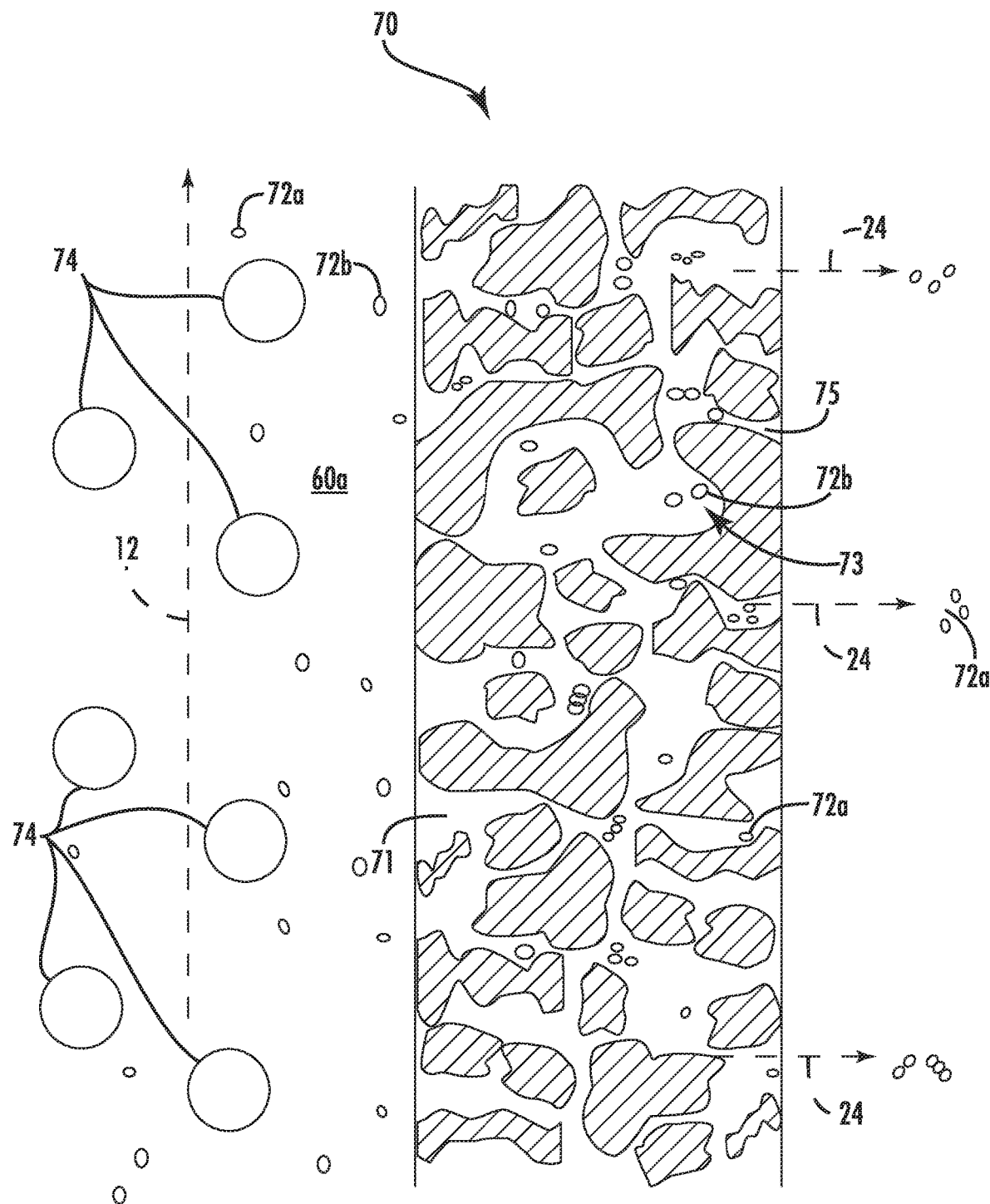
FIG. 2 is a schematic cross-sectional view of a wall of a hollow fiber within a tangential flow depth filter like that shown in FIG. 1A.

In this regard, FIG. 2 is a schematic cross-sectional illustration of a wall 70 of a hollow fiber 60 used in conjunction with a hollow fiber tangential flow filter 30 like that of FIG. 1A. In FIG. 2, a flow 12 comprising large particles 74, small particles 72a, and intermediate-sized particles 72b is introduced into the fluid inlet port 32a of the hollow fiber tangential flow filter 30. The large particles 74 pass along the inner surface of the wall 70 that forms the hollow fiber interior 60a (also referred to herein as the fiber lumen) of the hollow fibers and are ultimately released in the retentate flow. The wall 70 includes tortuous paths 71 that capture certain elements (i.e., intermediate-sized particles 72b) of the flow 12 as a portion of the flow 12 passes through the wall 70 of hollow fiber tangential flow filter 30 while allowing other particles (i.e., small particles 72a) to pass through the wall 70 as part of the permeate flow 24. In the schematic cross-sectional illustration of FIG. 2, settling zones 73 and narrowing channels 75 are illustrated as capturing intermediate-size particles 72b which enter the tortuous paths 71, while allowing smaller particles 72a to pass through the wall 70, thus trapping intermediate-size particles 72b and causing a separation of the intermediate-size particles 72b from smaller particles 72a in the permeate flow 24. This method is thus different from filtering obtained by the surface of standard thin wall hollow fiber tangential flow filter membranes, wherein intermediate-size particles 72b can build up at the inner surface of the wall 70, clogging entrances to the tortuous paths 71.

In this regard, one of the most problematic areas for various filtration processes, including filtration of cell culture fluids such as those filtered in perfusion and harvest of cell culture fluids, is decreased mass transfer of target molecules or particles due to filter fouling. The present disclosure overcomes many of these hurdles by combining the advantages of tangential flow filtration with the advantages of depth filtration. As in standard thin wall hollow fiber filters using tangential flow filtration, cells are pumped through the lumens of the hollow fibers, sweeping them along the surface of the inner surface of the hollow fibers, allowing them to be recycled for further production. However, instead of the protein and cell debris forming a fouling gel layer at the inner surface of the hollow fibers, the wall adds what is referred to herein as a "depth filtration" feature that traps the cell debris inside the wall structure, enabling increased volumetric throughput while maintaining close to 100% passage of typical target proteins in various embodiments of the disclosure. Such filters may be referred to herein as tangential flow depth filters.

As illustrated schematically in FIG. 2, tangential flow depth filters in accordance with various embodiments of the present disclosure do not have a precisely defined pore structure. Particles that are larger than the "pore size" of the filter will be stopped at the surface of the filter. A significant quantity of intermediate-sized particles, on the other hand, enter the wall for the filter, and are entrapped within the wall before emerging from the opposing surface of the wall. Smaller particles and soluble materials can pass though the filter material in the permeate flow. Being of thicker construction and higher porosity than many other filters in the art, the filters can exhibit enhanced flow rates and what is known in the filtration art as "dirt loading capacity," which is the quantity of particulate matter a filter can trap and hold before a maximum allowable back pressure is reached.

Despite a lack of a precisely defined pore structure, the pore size of a given filter can be objectively determined via a widely used method of pore size detection known as the "bubble point test." The bubble point test is based on the fact that, for a given fluid and pore size, with constant wetting, the pressure required to force an air bubble through a pore is inversely proportional to the pore diameter. In practice, this means that the largest pore size of a filter can be established by wetting the filter material with a fluid and measuring the pressure at which a continuous stream of bubbles is first seen downstream of the wetted filter under gas pressure. The point at which a first stream of bubbles emerges from the filter material is a reflection of the largest pore(s) in the filter material, with the relationship between pressure and pore size being based on Poiseuille's law which can be simplified to $P=K/d$, where P is the gas pressure at the time of emergence of the stream of bubbles, K is an empirical constant dependent on the filter material, and d is pore diameter. In this regard, pore sizes determined experimentally herein are measured using a POROLUX™ 1000 Porometer (Porometer NV, Belgium), based on a pressure scan method (where increasing pressure and the resulting gas flow are measured continuously during a test), which provides data that can be used to obtain information on the first bubble point size (FBP), mean flow pore size (MFP) (also referred to herein as "mean pore size"), and smallest pore size (SP). These parameters are well known in the capillary flow porometry art.

In various embodiments, hollow fibers for use in the present disclosure may have, for example, a mean pore size ranging from 0.1 microns (µm) or less to 30 microns or more, typically ranging from 0.2 to 5 microns, among other possible values.

In various embodiments, the hollow fibers for use in the present disclosure may have, for example, a wall thickness ranging from 1 mm to 10 mm, typically ranging from 2 mm to 7 mm, more typically about 5.0 mm, among other values.

In various embodiments, hollow fibers for use in the present disclosure may have, for example, an inside diameter (i.e., a lumen diameter) ranging from 0.75 mm to 13 mm, ranging from 1 mm to 5 mm, 0.75 mm to 5 mm, 4.6 mm, among other values. In general, a decrease in inside diameter will result in an increase in shear rate. Without wishing to be bound by theory, it is believed that an increase in shear rate will enhance flushing of cells and cell debris from the walls of the hollow fibers.

Hollow fibers for use in the present disclosure may have a wide range of lengths. In some embodiments, the hollow fibers may have a length ranging, for example, from 200 mm to 2000 mm in length, among other values.

The hollow fibers for use in the present disclosure may be formed from a variety of materials using a variety of processes.

For example, hollow fibers may be formed by assembling numerous particles, filaments, or a combination of particles and filaments into a tubular shape. The pore size and distribution of hollow fibers formed from particles and/or filaments will depend on the size and distribution of the particles and/or filaments that are assembled to form the hollow fibers. The pore size and distribution of hollow fibers formed from filaments will also depend on the density of the filaments that are assembled to form the hollow fibers. For example, mean pore sizes ranging from 0.5 microns to 50 microns may be created by varying filament density.

Suitable particles and/or filaments for use in the present disclosure include both inorganic and organic particles and/or filaments. In some embodiments, the particles and/or filaments may be mono-component particles and/or mono-component filaments. In some embodiments, the particles and/or filaments may be multi-component (e.g., bi-component, tri-component, etc.) particles and/or filaments. For example, bi-component particles and/or filaments having a core formed of a first component and a coating or sheath formed of a second component, may be employed, among many other possibilities.

In various embodiments, the particles and/or filaments may be made from polymers. For example, the particles and/or filaments may be polymeric mono-component particles and/or filaments formed from a single polymer, or they may be polymeric multi-component (i.e., bi-component, tri-component, etc.) particles and/or filaments formed from two, three, or more polymers. A variety of polymers may be used to form mono-component and multi-component particles and/or filaments including polyolefins such as polyethylene and polypropylene, polyesters such as polyethylene terephthalate and polybutylene terephthalate, polyamides such as nylon 6 or nylon 66, fluoropolymers such as polyvinylidene fluoride (PVDF) and polytetrafluoroethylene (PTFE), among others.

In various embodiments, a porous wall of a filter may have a density that is a percentage of volume that the filaments take up compared to an equivalent solid volume of the polymer. For example, a percent density may be calculated by dividing the mass of the porous wall of the filter by the volume that the porous wall takes up and comparing the result, in ratio form, to the mass of a non-porous wall of the filament material divided by the same volume. A filter having a specific density percentage may be produced during manufacturing that has a direct relation to the amount of variable cell density (VCD) at which the filter can operate without fouling. A density of a porous wall of a filter may additionally or alternatively be expressed by a mass per volume (e.g., grams/cm3).

Particles may be formed into tubular shapes by using, for example, tubular molds. Once formed in a tubular shape, particles may be bonded together using any suitable process. For instance, particles may be bonded together by heating the particles to a point where the particles partially melt and become bonded together at various contact points (a process known as sintering), optionally, while also compressing the particles. As another example, the particles may be bonded together by using a suitable adhesive to bond the particles to one another at various contact points, optionally, while also compressing the particles. For example, a hollow fiber having a wall analogous to the wall 70 that is shown schematically in FIG. 2 may be formed by assembling numerous irregular particles into a tubular shape and bonding the particles together by heating the particles while compressing the particles.

Filament-based fabrication techniques that can be used to form tubular shapes include, for example, simultaneous extrusion (e.g., melt-extrusion, solvent-based extrusion, etc.) from multiple extrusion dies, or electrospinning or electrospraying onto a rod-shaped substrate (which is subsequently removed), among others.

Filaments may be bonded together using any suitable process. For instance, filaments may be bonded together by heating the filaments to a point where the filaments partially melt and become bonded together at various contact points, optionally, while also compressing the filaments. As another example, filaments may be bonded together by using a suitable adhesive to bond the filaments to one another at various contact points, optionally while also compressing the filaments.

In particular embodiments, numerous fine extruded filaments may be bonded together to at various points to form a hollow fiber, for example, by forming a tubular shape from the extruded filaments and heating the filaments to bond the filaments together, among other possibilities.

In some instances, the extruded filaments may be melt-blown filaments. As used herein, the term "melt-blown" refers to the use of a gas stream at an exit of a filament extrusion die to attenuate or thin out the filaments while they are in their molten state. Melt-blown filaments are described, for example, in U.S. Pat. No. 5,607,766 to Berger. In various embodiments, mono- or bi-component filaments are attenuated as they exit an extrusion die using known melt-blowing techniques to produce a collection of filaments. The collection of filaments may then be bonded together in the form of a hollow fiber.

In certain beneficial embodiments, hollow fibers may be formed by combining bicomponent filaments having a sheath of first material which is bondable at a lower temperature than the melting point of the core material. For example, hollow fibers may be formed by combining bicomponent extrusion technology with melt-blown attenuation to produce a web of entangled biocomponent filaments, and then shaping and heating the web (e.g., in an oven or using a heated fluid such as steam or heated air) to bond the filaments at their points of contact. An example of a sheath-core melt-blown die is schematically illustrated in U.S. Pat. No. 5,607,766 in which a molten sheath-forming polymer and a molten core-forming polymer are fed into the die and extruded from the same. The molten bicomponent sheath-core filaments are extruded into a high velocity air stream, which attenuates the filaments, enabling the production of fine bicomponent filaments. U.S. Pat. No. 3,095,343 to Berger shows an apparatus for gathering and heat-treating a multi-filament web to form a continuous tubular body (e.g., a hollow fiber) of filaments randomly oriented primarily in a longitudinal direction, in which the body of filaments are, as a whole, longitudinally aligned and are, in the aggregate, in a parallel orientation, but which have short portions running more or less at random in non-parallel diverging and converging directions. In this way, a web of sheath-core bicomponent filaments may be pulled into a confined area (e.g., using a tapered nozzle having a central passageway forming member) where it is gathered into tubular rod shape and heated (or otherwise cured) to bond the filaments.

In certain embodiments, as-formed hollow fiber may be further coated with a suitable coating material (e.g., PVDF) either on the inside or outside of the fiber, which coating process may also act to reduce the pore size of the hollow fiber, if desired.

Hollow fibers such as those described above may be used to construct tangential flow filters for bioprocessing and pharmaceutical applications. Examples of bioprocessing applications in which such tangential flow filters may be employed include those where cell culture fluid is processed to separating cells from smaller particles such as proteins, viruses, virus like particles (VLPs), exosomes, lipids, DNA and other metabolites.

Such applications include perfusion applications in which smaller particles are continuously removed from cell culture medium as a permeate fluid while cells are retained in a retentate fluid returned to a bioreactor (and in which equivalent volumes of media are typically simultaneously added to the bioreactor to maintain overall reactor volume). Such applications further include clarification or harvest applications in which smaller particles (typically biological products) are more rapidly removed from cell culture medium as a permeate fluid.

Hollow fibers such as those described above may be used to construct tangential flow depth filters for particle fractionation, concentration and washing. Examples of applications in which such tangential flow filters may be employed include the removal of small particles from larger particles using such tangential flow depth filters, the concentration of microparticles using such tangential flow depth filters and washing microparticles using such tangential flow filters.

A specific example of a bioreactor system 10 for use in conjunction with the present disclosure will now be described. With reference to FIGS. 3, 4A and 4B, the bioreactor system 10 includes a bioreactor vessel 11 containing bioreactor fluid 13, a tangential flow filtering system 14, and a control system 20. The tangential flow filtering system 14 is connected between a bioreactor outlet 11a and bioreactor inlet 11b to receive bioreactor fluid 12 (also referred to as a bioreactor feed), which contains, for example, cells, cell debris, cell metabolites including waste metabolites, expressed proteins, etc., through bioreactor tubing 15 from the bioreactor 11 and to return a filtered flow 16 (also referred to as a retentate flow or bioreactor return) through return tubing 17 to the bioreactor 11. The bioreactor system 10 cycles bioreactor fluid through the tangential flow filtering system 14 which removes various materials (e.g., cell debris, soluble and insoluble cell metabolites and other products produced by cells including expressed proteins, viruses, virus like particles (VLPs), exosomes, lipids, DNA, or other small particles) from the bioreactor fluid and returns cells to allow the reaction in the bioreactor vessel 11 to continue. Removing waste metabolites allows the continued proliferation of cells within the bioreactor, thereby allowing the cells to continue to express recombinant proteins, antibodies or other biological materials that are of interest.

The bioreactor tubing 15 may be connected, for example, to the lowest point or dip tube of the bioreactor 11 and the return tubing 17 may be connected to the bioreactor 11, for example, in the upper portion of the bioreactor volume and submerged in the bioreactor fluid 13.

The bioreactor system 10 includes an assembly comprising a hollow fiber tangential flow filter 30 (described in more detail above), a pump 26, and associated fittings and connections. Any suitable pump may be used in conjunction with the present disclosure including, for example, peristaltic pumps, positive displacement pumps, and pumps with levitating rotors inside the pumpheads, among others. As a specific example, the pump 26 may include a low shear, gamma-radiation stable, disposable, levitating pumphead 26a, for example, a model number PURALEV® 200SU low shear re-circulation pump manufactured by Levitronix, Waltham, Mass., USA. The PURALEV® 200SU includes a magnetically levitated rotor inside a disposable pumphead, and stator windings in the pump body, allowing simple removal and replacement of the pumphead 26a.

The flow of bioreactor fluid 12 passes from the bioreactor vessel 11 to the tangential flow filtering system 14 and the return flow of the bioreactor fluid 16 passes from the tangential flow filtering system 14 back to the bioreactor vessel 11. A permeate flow 24 (e.g., containing soluble and insoluble cell metabolites and other products produced by cells including expressed proteins, viruses, virus like particles (VLPs), exosomes, lipids, DNA, or other small particles) is stripped from the flow of bioreactor material 12 by the tangential flow filtering system 14 and carried away from the tangential flow filtering system 14 by tubing 19. The permeate flow 24 is drawn from the hollow fiber tangential flow system 14 by a permeate pump 22 into a storage container 23.

In the embodiment shown, the tangential flow filtering system 14 (see FIG. 4A) includes a disposable pumphead 26a, which simplifies initial set up and maintenance. The pumphead 26a circulates the bioreactor fluid 12 through the hollow fiber tangential flow filter 30 and back to the bioreactor vessel 11. A non-invasive transmembrane pressure control valve 34 may be provided in line with the flow 16 from the hollow fiber tangential flow filter 30 to the bioreactor vessel 11, to control the pressure within the hollow fiber tangential flow filter 30. For example, the valve 34 may be a non-invasive valve, which resides outside tubing carrying the return flow 16 that squeezes the tubing to restrict and control the flow, allowing the valve to regulate the applied pressure on the membrane. Alternatively, or in addition, a flow controller 36 may be provided at the pumphead 26a inlet in order to provide pulsed flow to the hollow fiber tangential flow filter 30, as described in more detail below. The permeate flow 24 may be continually removed from the bioreactor fluid 13 which flows through the hollow fiber tangential flow filter 30. The pumphead 26a and the permeate pump 22 are controlled by the control system 20 to maintain the desired flow characteristics through the hollow fiber tangential flow filter 30.

The pumphead 26a and hollow fiber tangential flow filter 30 in the tangential flow filtering system 14 may be connected by flexible tubing allowing easy changing of the elements. Such tubing allows aseptic replacement of the hollow fiber tangential flow filter 30 in the event that the hollow fiber tangential flow filter 30 becomes plugged with material and therefore provides easy exchange to a new hollow fiber assembly.

The tangential flow filtering system 14 may be sterilized, for example, using gamma irradiation, ebeam irradiation, or ETO gas treatment.

Referring again to FIG. 1, during operation, two permeate fluid outlet ports 32b and 32c may be employed to remove permeate flow 24 in in some embodiments. In other embodiments, only a single permeate fluid outlet port may be employed. For example, permeate flow 24 may be collected from the upper permeate port 32c only (e.g., by closing permeate port 32b) or may be collected from the lower permeate port 32b only (e.g., by draining the permeate flow 24 from the lower permeate port 32b while the permeate port 32c closed or kept open). In certain beneficial embodiments, the permeate flow 24 may be drained from the lower permeate port 32b to reduce or eliminate Sterling flow, which is a phenomenon where an upstream (lower) end of the of the hollow fibers 60 (the high-pressure end) generates permeate that back-flushes the downstream (upper) end of the hollow fibers 60 (the low-pressure end). Draining the permeate flow 24 from the lower permeate port 32b leaves air in contact with the upper end of the of the hollow fibers 60 minimizing or eliminating Sterling flow.

In certain embodiments, the bioreactor fluid 12 may be introduced into the hollow fiber tangential flow filter 30 at a constant flow rate.

In certain embodiments, the bioreactor fluid may be introduced into the hollow fiber tangential flow filter 30 in a pulsatile fashion (i.e., under pulsed flow conditions), which has been shown to increase permeate rate and volumetric throughput capacity. As used herein "pulsed flow" is a flow regime in which the flow rate of a fluid being pumped (e.g., fluid entering the hollow fiber tangential flow filter) is periodically pulsed (i.e., the flow has periodic peaks and troughs). In some embodiments, the flow rate may be pulsed at a frequency ranging from 1 cycle per minute or less to 2000 cycles per minute or more (e.g., ranging from 1 to 2 to 5 to 10 to 20 to 50 to 100 to 200 to 500 to 1000 to 2000 cycles per minute) (i.e., ranging between any two of the preceding values). In some embodiments, the flow rate associated with the troughs is less than 90% of the flow rate associated with the peaks, less than 75% of the flow rate associated with the peaks, less than 50% of the flow rate associated with the peaks, less than 25% of the flow rate associated with the peaks, less than 10% of the flow rate associated with the peaks, less than 5% of the flow rate associated with the peaks, or even less than less than 1% of the flow rate associated with the peaks, including zero flow and periods of backflow between the pulses.

Pulsed flow may be generated by any suitable method. In some embodiments, pulsed flow may be generated using a pump such as a peristaltic pump that inherently produces pulsed flow. For example, tests have been run by applicant which show that switching from a pump with a magnetically levitated rotor like that described above under constant flow conditions to a peristaltic pump (which provides a pulse rate of about 200 cycles per minute) increases the amount of time that a tangential flow depth filter can be operated before fouling (and thus increases the quantity of permeate that can be collected).

In some embodiments, pulsed flow may be generated using pumps that otherwise provide a constant or essentially constant output (e.g., a positive displacement pump, centrifugal pumps including magnetically levitating pump, etc.) by employing a suitable flow controller to control the flow rate. Examples of such flow controllers include those having electrically controlled actuators (e.g. a servo valve or solenoid valve), pneumatically controlled actuators or hydraulically controlled actuators to periodically restrict fluid entering or exiting the pump. For example, in certain embodiments, a flow controller 36 may be placed upstream (e.g., at the inlet) or downstream (e.g., at the outlet) of a pump 26 like that described hereinabove (e.g., upstream of pumphead 26a in FIG. 4A) and controlled by a controller 20 to provide pulsatile flow having the desired flow characteristics.

EXAMPLES

Tangential flow depth filters were tested which contained hollow fibers having a lumen diameter of 1.5 mm and a wall thickness of 2.4 mm. However, other ranges of lumen diameters are contemplated throughout this disclosure. Hollow fibers having a mean pore size of 1 micron or 2 microns were formed from bonded extruded bicomponent filaments having a core of polyethylene terephthalate and a sheath of polypropylene. Hollow fibers having a mean pore size of 0.5 micron, 1 micron, 2 microns or 4 microns were also formed from bonded extruded bicomponent filaments having a core of polyethylene terephthalate and a sheath of polypropylene, which were subsequently provided with a coating of polyvinylidene fluoride (PVDF).

A fluid containing Chinese Hamster Ovary (CHO) cells was concentrated by recycling the fluid though tangential flow depth filters containing hollow filters as described above using a peristaltic pump providing a pulsatile flow at a pulse frequency of 200 cycles per minute. Runs were conducted in concentration mode at 8000 s−1 shear rate (160 ml/min) using tangential flow depth filters having the following hollow fibers with the following permeation flow rates, expressed as LMH (liters per meter2 per hour, or L/m2/h): (a) 1 micron noncoated hollow fiber, 300 LMH, (b) 2 micron noncoated hollow fiber, 100 LMH, (c) 2 micron uncoated hollow fiber, 300 LMH, (d) 2 micron coated hollow fiber, 100 LMH, and (e) 4 micron coated hollow fiber, 40 LMH increased to 100 LMH during run.

Figure 5A:
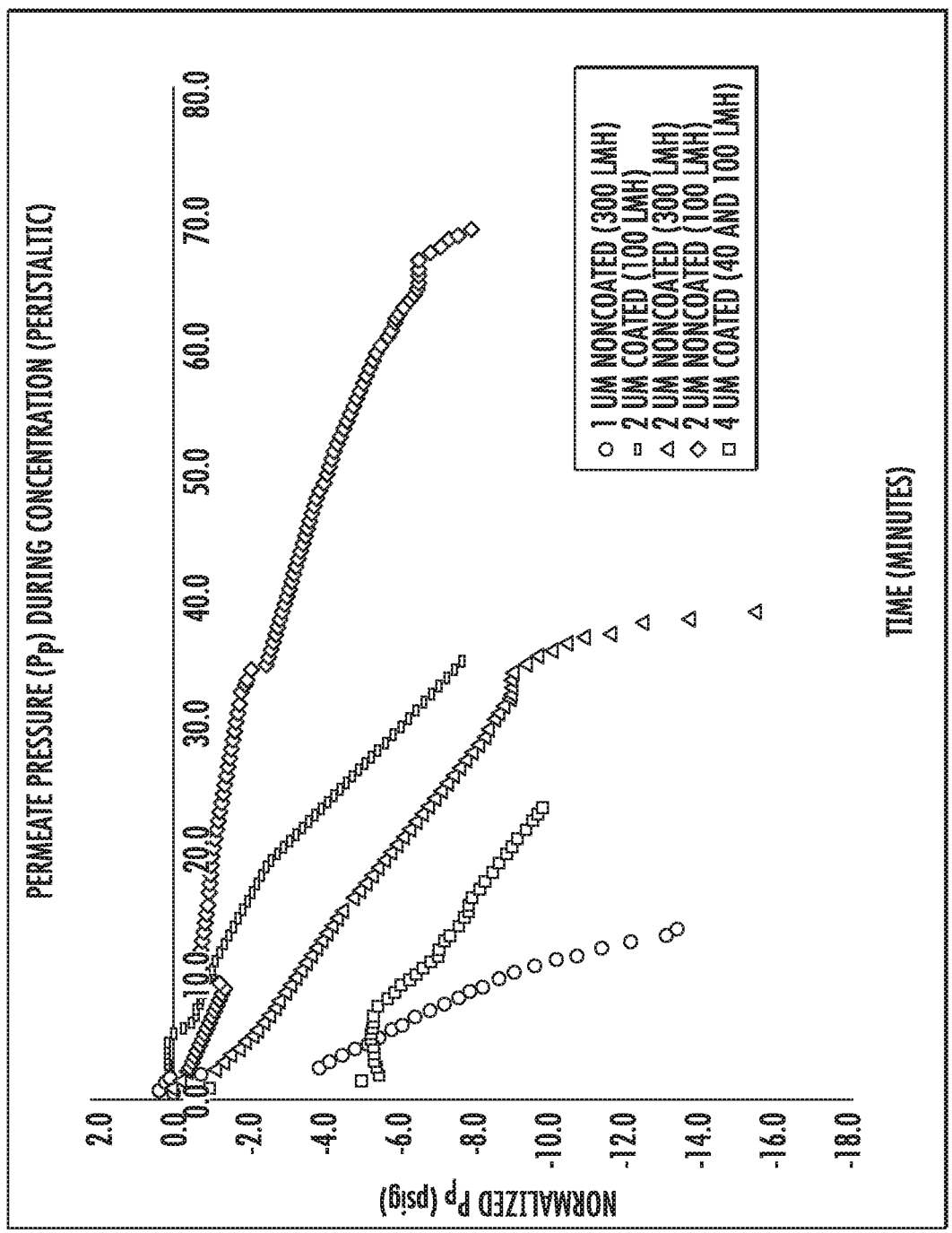
FIGS. 5A and 5B show normalized permeate pressure versus time for various tangential flow filtering systems according to the present disclosure.

Results expressed as normalized permeate pressure versus time are shown in FIG. 5A. Final concentrations of cells in the retentate at the point of filter fouling were as follows: 115·106 cells/ml (1 μm noncoated, 300 LMH); 97·106 cells/ml (2 μm coated, 100 LMH,); 688·106 cells/ml (2 μm noncoated, 300 LMH); 1.5·109 cells/ml (2 μm noncoated, 100 LMH); and 72·106 cells/ml (4 μm coated, 40 and 100 LMH).

As seen from FIG. 5A, generally, pressure decay was quick at 300 LMH and for the 4 μm fiber. 100 LMH appeared to be the most optimal for concentration. Among the 2 μm fibers, the coated 2 μm fiber performed worse than the noncoated 2 μm fiber at 100 LMH. Each of the fibers of FIG. 5A has a percent density. The 1 μm fiber has a percent density of about 55%, the 2 μm fiber has a percent density of about 53%, the 4 μm filter has a density of about 51%. The 2 μm 53% density fibers performed better than both of the 1 μm 55% density and 4 μm 51% density fibers, with the 1 μm 55% density fiber performing the worst of these samples. Exemplary undesirable characteristics observed of these fibers include passing too much turbidity and too many cells through the 4 μm 51% density fiber and a passage of fluid through the 1 μm 55% density at an undesirably rapid rate.

Figure 5B:
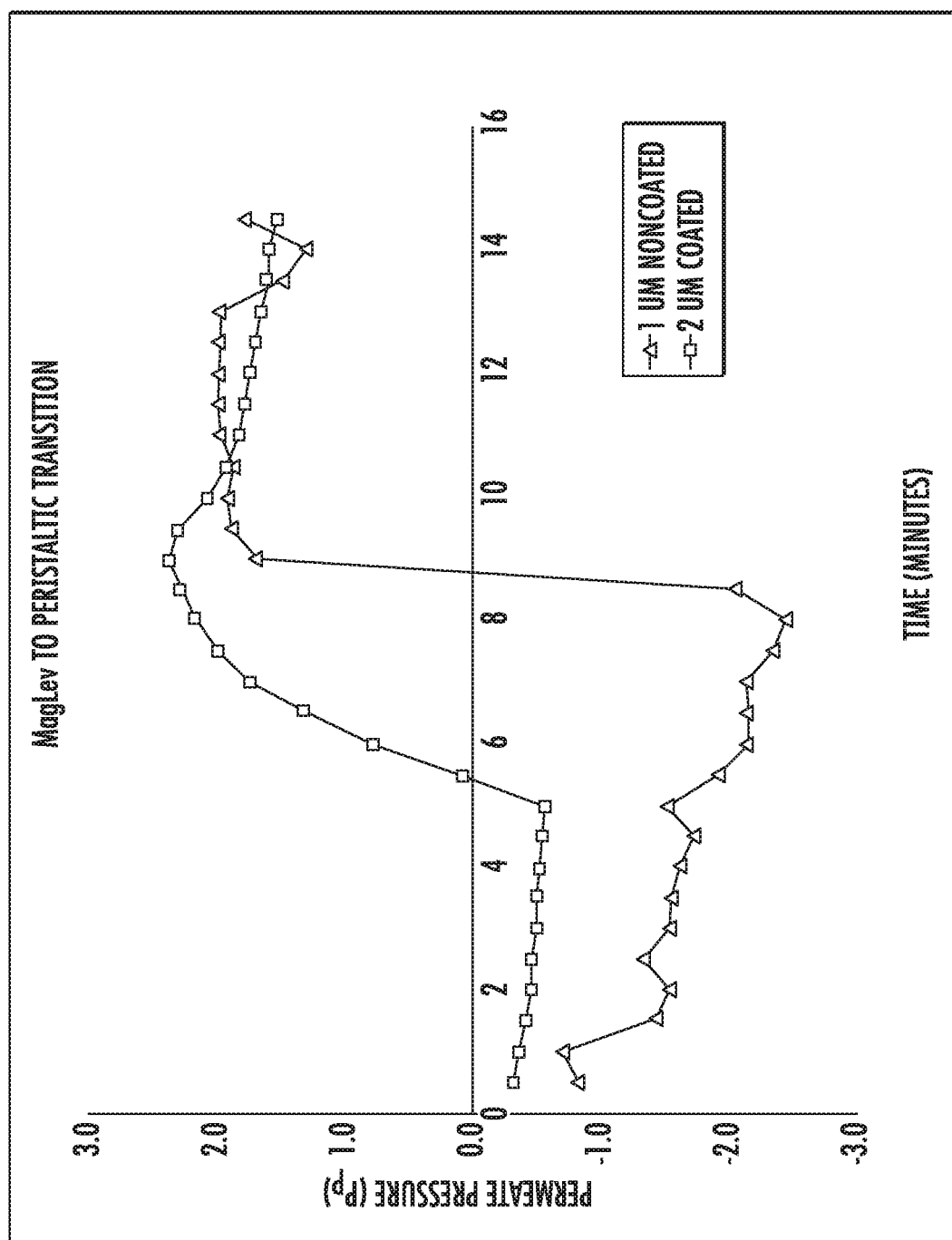

A fluid containing Chinese Hamster Ovary (CHO) cells was also concentrated by initially pumping the fluid through the tangential flow depth filter using a magnetically levitating pump having the following hollow fibers at the following flow rates: 1 micron noncoated hollow fiber, 100 LMH and 2 micron coated hollow fiber, 100 LMH. Flow was switched from the magnetically levitating pump to a peristaltic pump providing a pulsatile flow at a pulse frequency of 200 cycles per minute after about 5 minutes for the 2 micron coated hollow fiber and after about 8 minutes for the 1 micron noncoated hollow fiber. Results expressed as normalized permeate pressure versus time are shown in FIG. 5B. As seen from FIG. 5B, normalized permeate pressure was negative for the filters during the initial periods of operation using the magnetically levitating pump. After switching the peristaltic pump, however, the normalized permeate pressure turned positive, accompanied by an increase in permeate flow.

While the disclosure herein disclosed has been described by means of specific embodiments and applications thereof, numerous modifications and variations could be made thereto by those skilled in the art without departing from the scope of the disclosure set forth in the claims.

Figure 6:
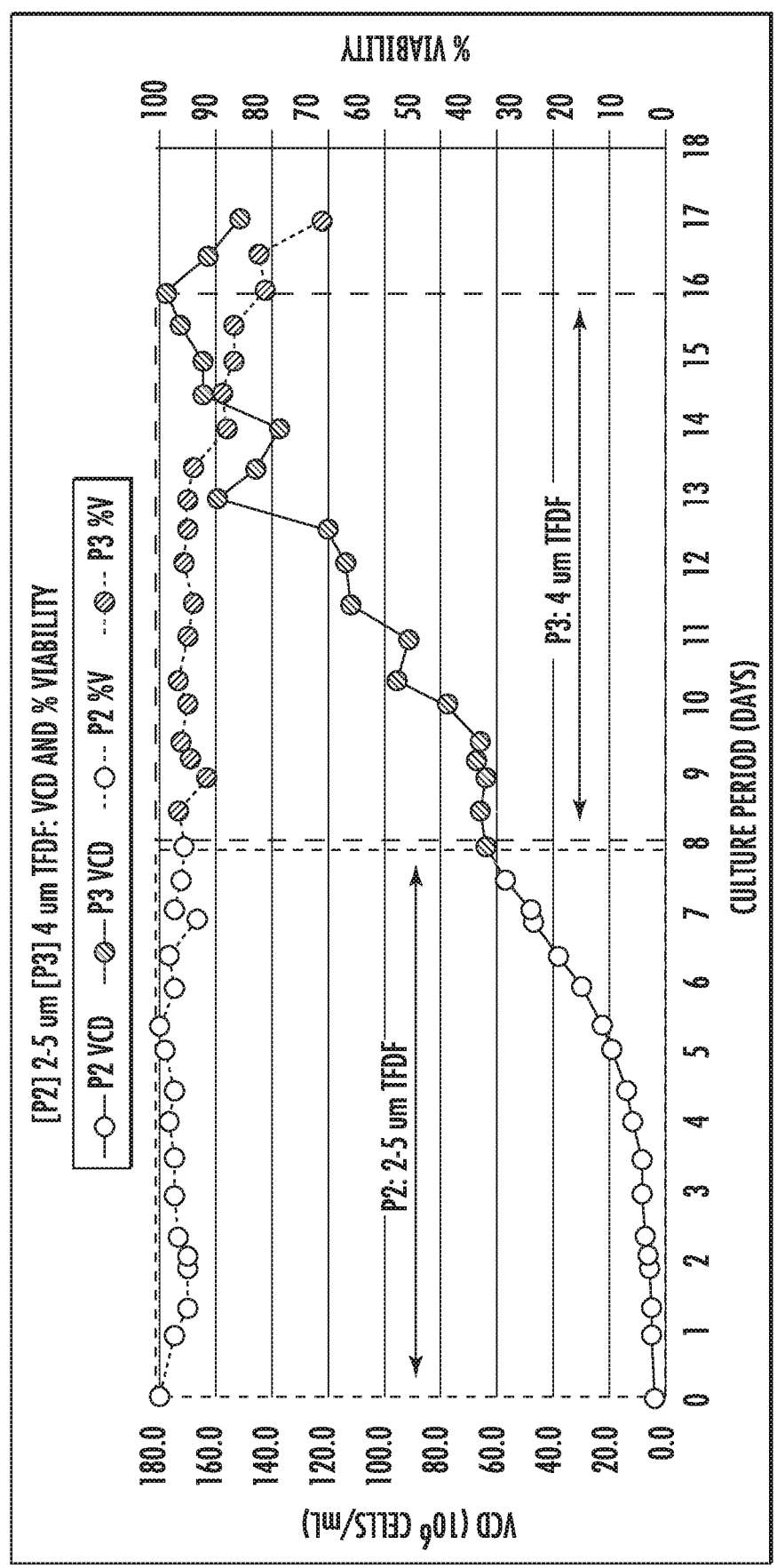
FIG. 6 shows viable cell density (VCD) and percent viability over time for perfusion filters, according to an embodiment of the present disclosure.

With reference to FIG. 6, data for VCD and percent viability over time for an embodiment of a tangential flow filter for bioprocessing applications is shown, which includes a procedure initiated while using a first sintered filter P2 having a range of pore sizes of about 2 μm to about 5 μm, followed by a second filter P3 replacing the first filter P2. The second filter P3 had pore sizes of about 4 μm and a density percentage of about 51%. The first sintered filter P2 fouled during a procedure after about eight days of operation. During this eight-day operation, the first sintered filter P2 was unable to operate with more than a VCD of about 60×106 cells/mL. After fouling, the first sintered filter P2 was replaced with the second filter P3. The second filter P3 was exposed to more than 60×106 cells/mL for an operation period of nine days with a 2 vessel volumes per day (VVD) exchange rate. A peak VCD of the system during operation with the second filter P3 was 175.0×106 cells/mL. On the ninth day of the second filter's P3 operation (seventeenth day for the procedure overall) the permeate line of the system experienced a mechanical failure and began leaking. Therefore, the procedure was terminated. The second filter P3 maintained a larger VCD during its operation compared to the first sintered filter P2.

Table 1 below shows exemplary data of six filters having a density percentage of about 51%. Although the second filter P3 of FIG. 6 and the filters of Table 1 below have a pore size of about 4 μm and a density percentage of about 51%, other filters are contemplated having a different pore size and density percentage, e.g., a filter having a density percentage of about 53% and a pore size of about 2 μm with a 90% nominal retention.

With reference to FIG. 7, various metrics of a filter of FIG. 6 are shown. For example, an average percent of sieving through the second filter P3 is 99.24+14.85. Percent sieving refers to the volume of a fluid that transfers through (e.g., across) a porous wall of a filter. The second filter's P3 peak VCD of 175.0×106 cells/mL is much higher than that of the first sintered filter P2 of about 60×106 cells/mL, which was achieved without the second filter P3 fouling while the first sintered filter P2 did foul.

Figure 8:
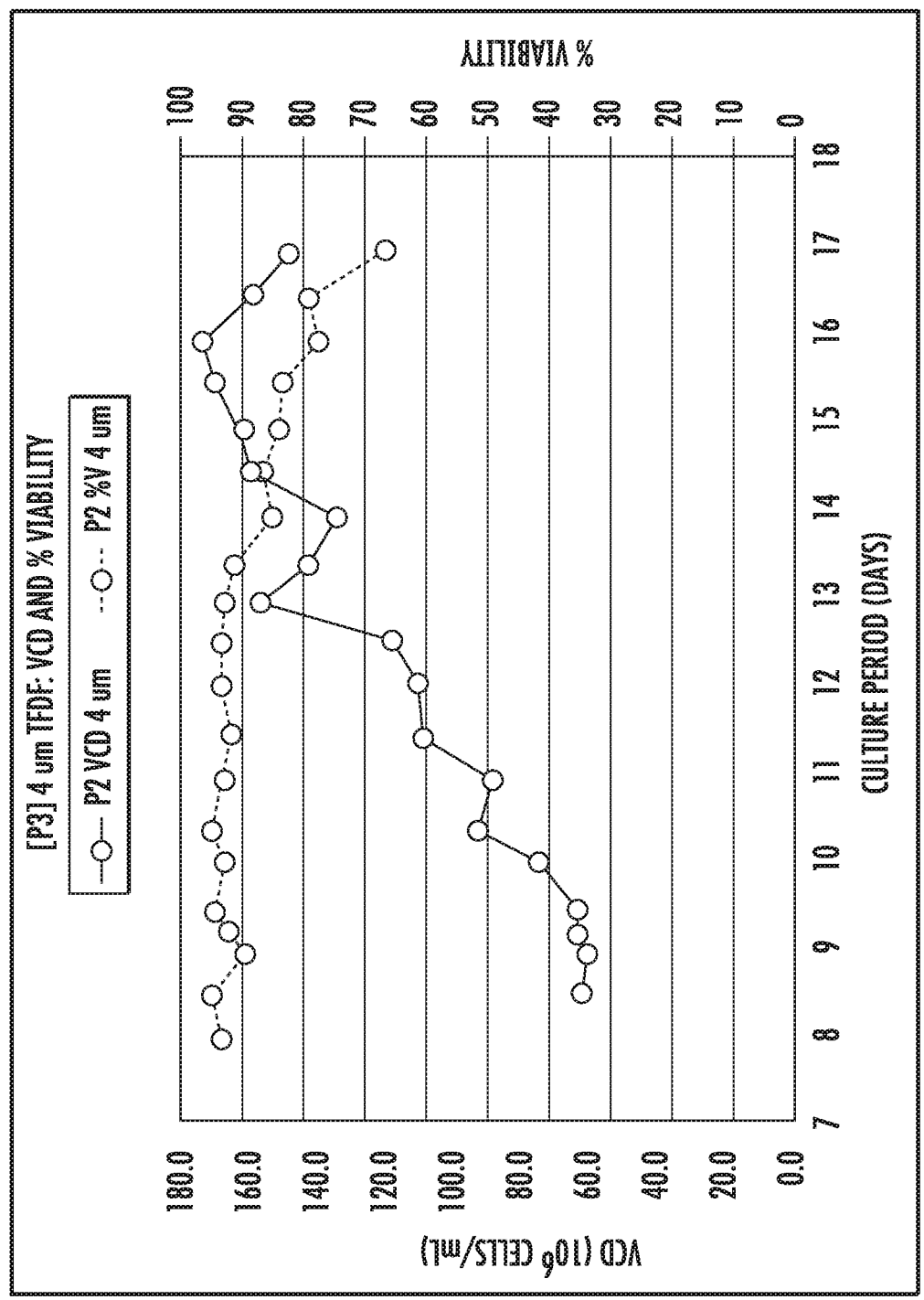
FIG. 8 shows a cell growth profile of a filter of FIGS. 6 and 7.

With reference to FIG. 8, a cell growth profile of the second filter P3 of FIGS. 6 and 7 is shown. The VVD range of the second filter P3 is 2. A VVD range and peak VCD of the second filter P3 is displayed in Table 2.

TABLE 2

| VVD Range and Peak VCD of the Second Filter P3 | | |
|---|---|---|
| | VVD Range | Peak VCD ($10^6$ cells/mL) |
| P3 | 2 | 175.0 |

Figure 9:
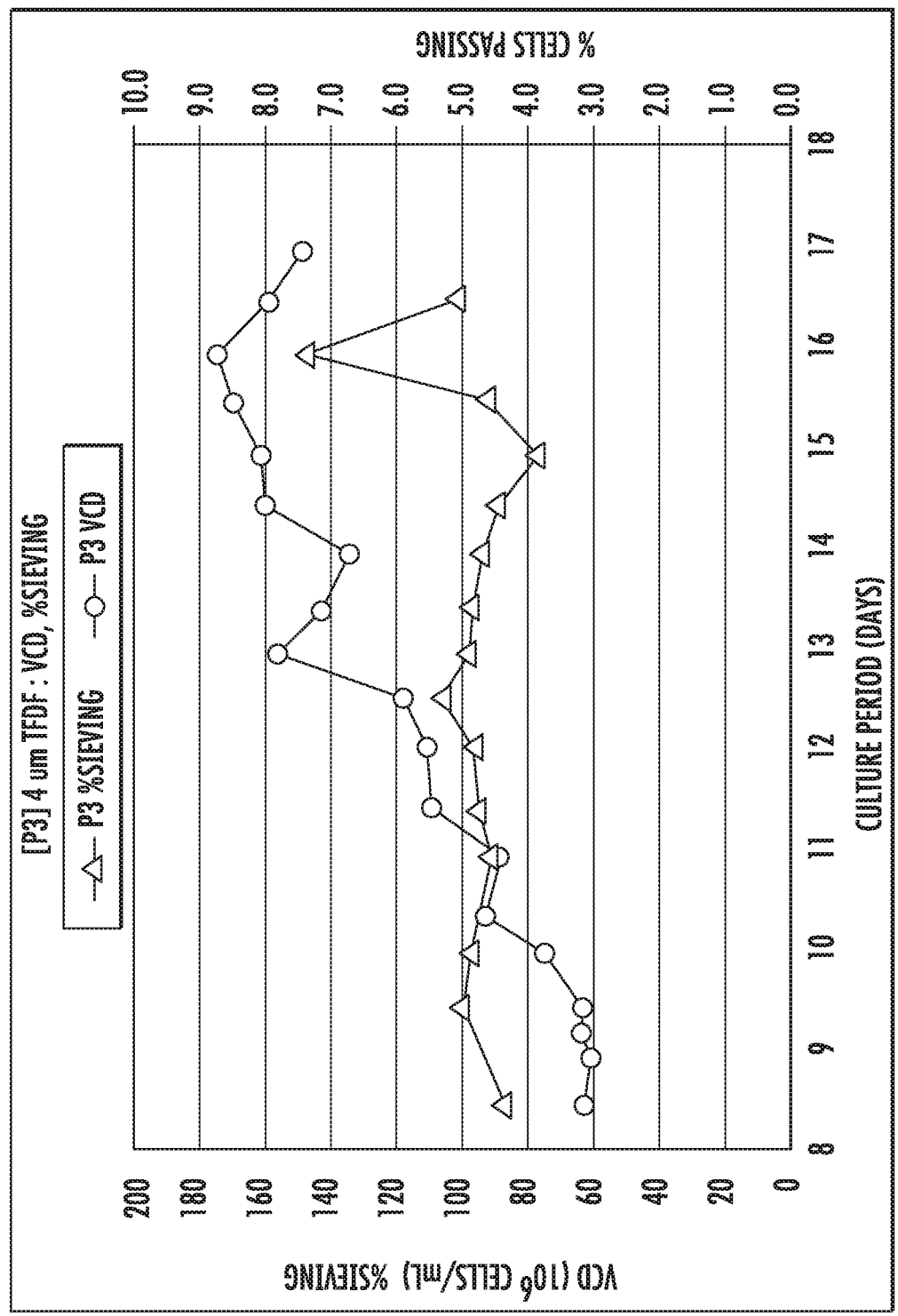
FIG. 9 shows an average percent of sieving for a filter of FIGS. 6-8.

FIG. 9 and Table 3 show an average percent of sieving for the second filter P3 of FIGS. 6-8. The second filter P3 exhibited an average percent sieving of about 100% and maintained above about 80% throughout its operation.

TABLE 3

| Average Percent Sieving of the Second Filter P3 | |
|---|---|
| | Avg % Sieving |
| P3 | 99.24% ± 14.85% |

Figure 10:
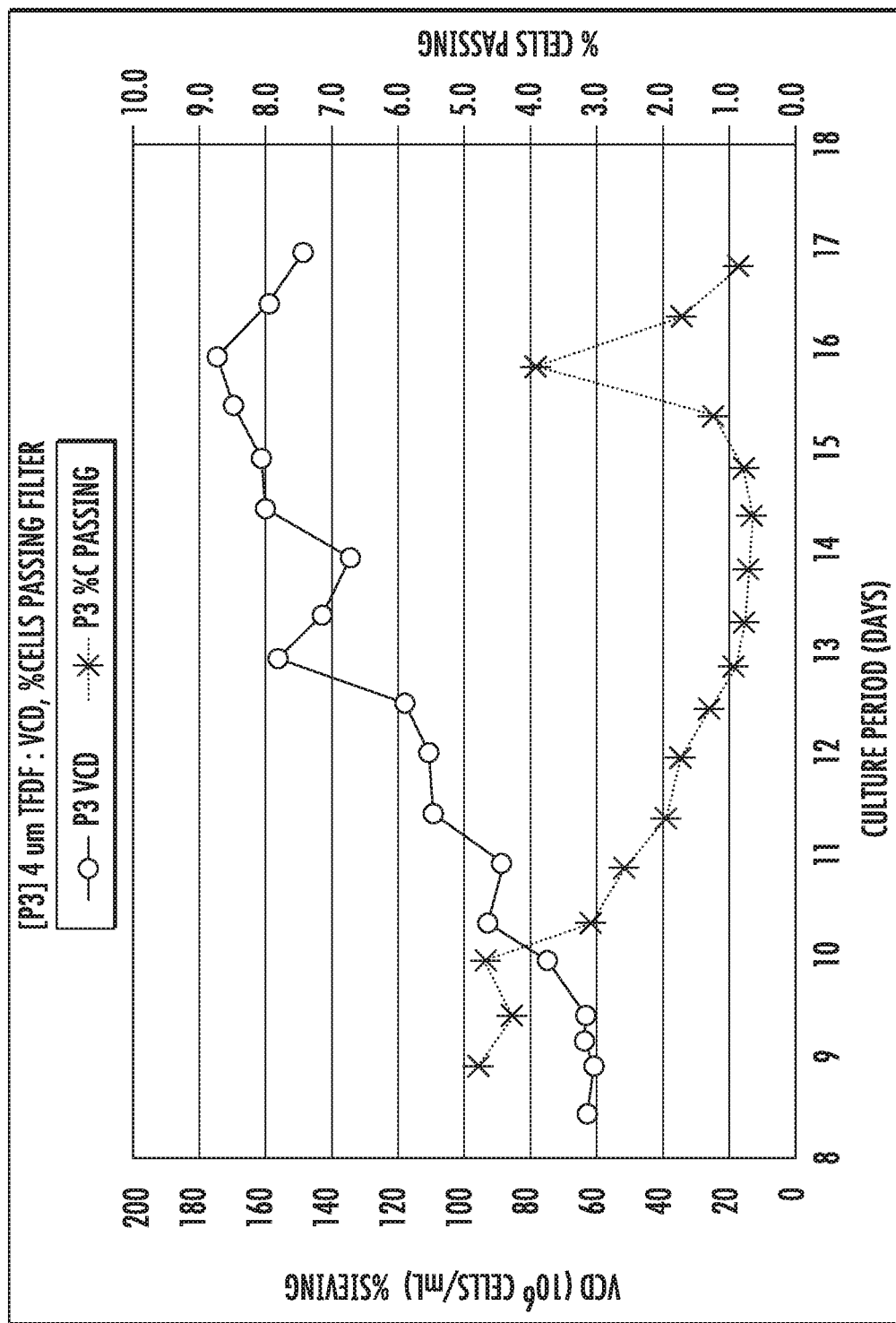
FIG. 10 shows a percent of cells passing through a filter of FIGS. 6-9.

FIG. 10 and Table 4 show a percent of cells passing through the second filter P3 of FIGS. 6-9. The initial percent of cells passing through the second filter P3 was initially much higher (about more than 1%) than usual values observed in previous TFDF perfusion (e.g., less than about 1%). The percent of cells passing decreased over the perfusion period of the second filter P3, with a spike in cells passing at the peak VCD. Cell Retention efficiency was maintained above about 95% throughout perfusion culture.

TABLE 4

| Passage of Cells Through the Second Filter P3 | | | | |
|---|---|---|---|---|
| Peak % Cells Passing | Peak VCD Passing | Avg % Cells Passing | Avg VCD Passing | Avg CD (um) |
| P3 4.79% | 6.87 | 2.10% ± 1.49% | 2.26 ± 1.42 | 10.13 ± 0.28 |

TABLE 1

| Parameters for Filters Having a Pore Size of About 4 μm Scale (sn B651486632) Caliper (SN 11344515) | | | | | | | |
|---|---|---|---|---|---|---|---|
| Sample | Weight (g) | Length (in) | OD (cm) max | OD (cm) min | Avg | ID (cm) | Density |
| 1 | 10.7 | 27.3 | 0.63246 | 0.62992 | 0.63119 | 0.15 | 0.522931121 |
| 2 | 13 | 33.46 | 0.64262 | 0.63246 | 0.63754 | 0.15 | 0.507494299 |
| 3 | 13 | 33.42 | 0.6477 | 0.63246 | 0.64008 | 0.15 | 0.503843298 |
| 4 | 5.8 | 14.88 | 0.64008 | 0.63246 | 0.63627 | 0.15 | 0.511296131 |
| 5 | 5.8 | 14.88 | 0.63754 | 0.62992 | 0.63373 | 0.15 | 0.515646644 |
| 6 | 5.9 | 14.88 | 0.635 | 0.63246 | 0.63373 | 0.15 | 0.524537103 |
| | | | | | | Avg | 0.514291433 |
| | | | | | | StDev | 0.00831614 |

Figure 11:
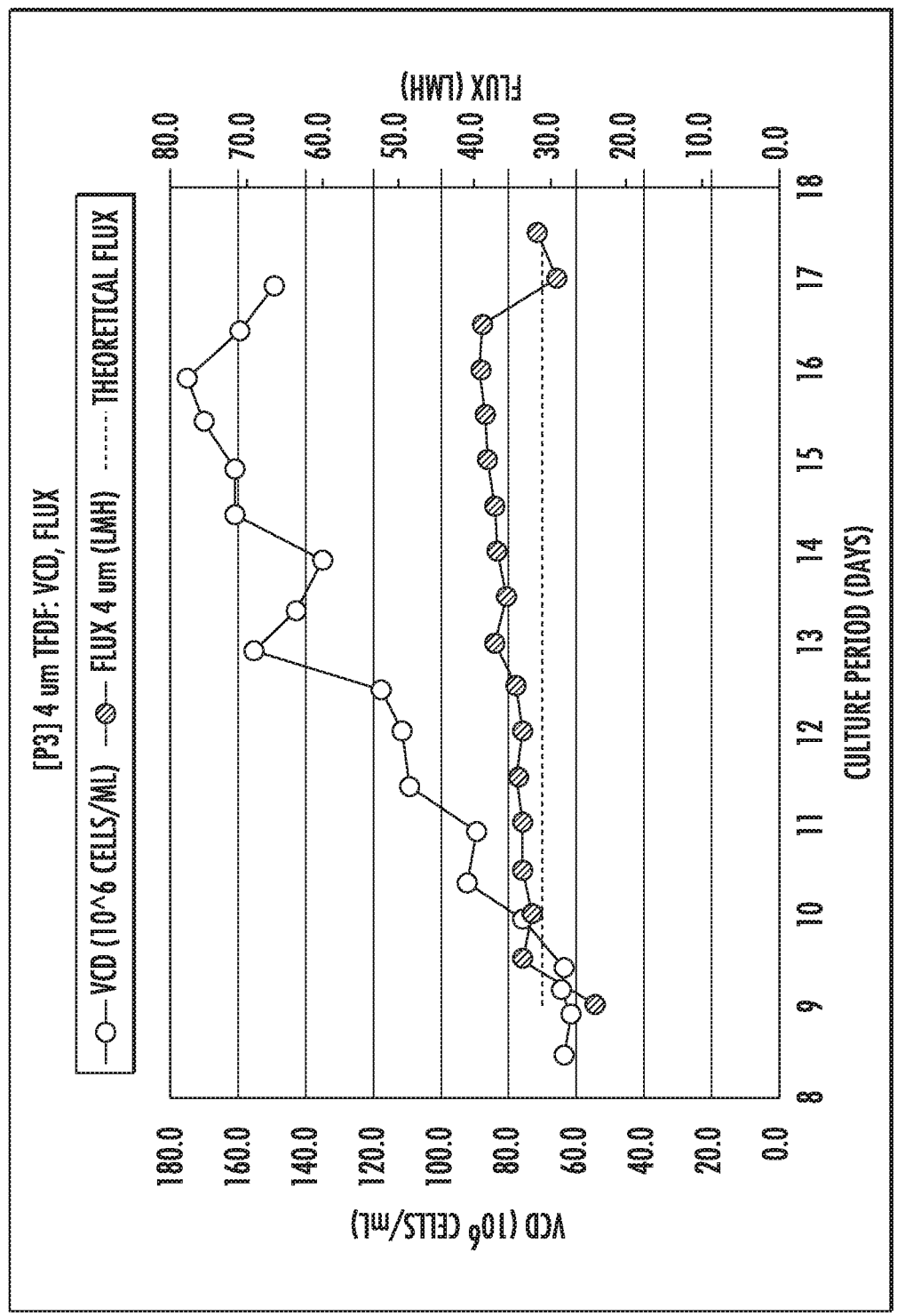
FIG. 11 shows a flux of a filter of FIGS. 6-10.

FIG. 11 and Table 5 show a flux of the second filter P3 run continuously using a peristaltic pump of FIGS. 6-10, which is significantly linear across the culture period.

TABLE 5

Flux of the Second Filter P3

| | VVD Range | Flux Range (LMH) |
|---|---|---|
| P3 | 2 | 24-39 |

Figure 12:
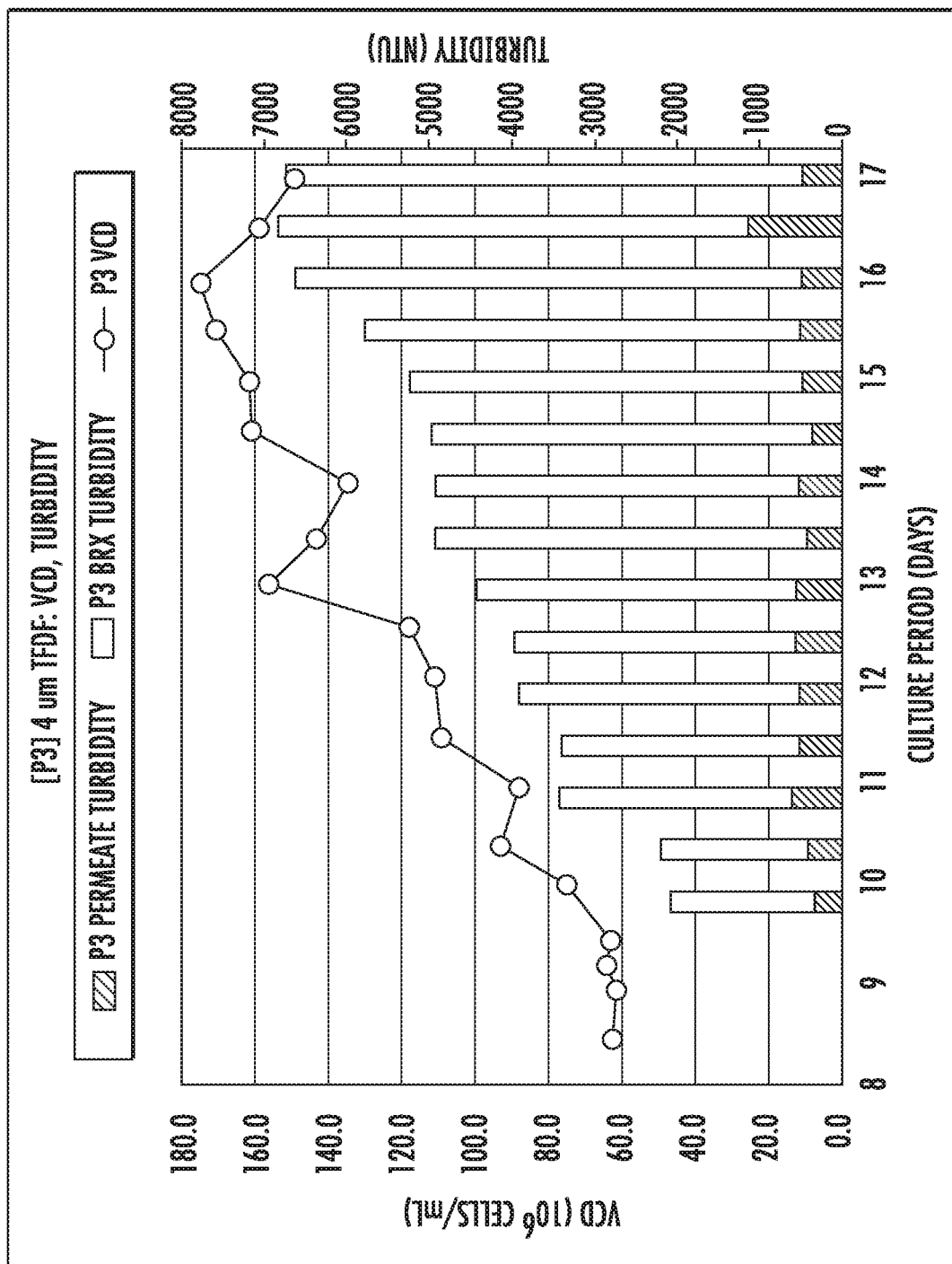
FIG. 12 shows a turbidity of a filter of FIGS. 6-11.

FIG. 12 and Table 6 show a turbidity of the second filter P3 of FIGS. 6-11. Turbidity values related to the second filter P3 were higher than the first filter P2.

TABLE 6

Turbidity of the Second Filter P3

| | Retentate Range (NTU) | Permeate Range (NTU) |
|---|---|---|
| P3 | 1720-625 | 354-1139 |

Figure 13:
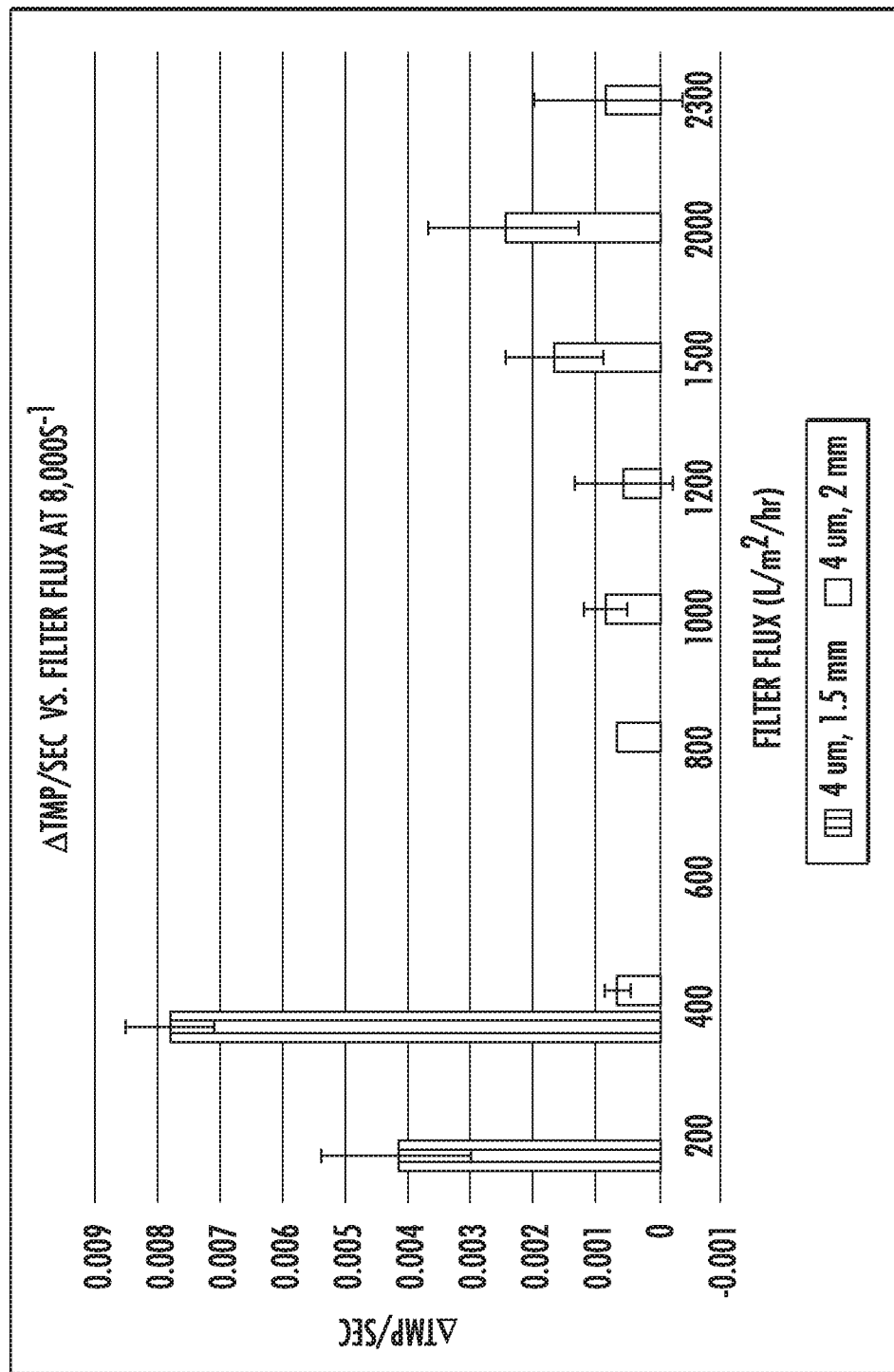
FIG. 13 shows an empirical comparison of transmembrane pressure change and filter flux for two TFDF systems of the present disclosure.

With reference to FIG. 13, transmembrane pressure (ΔTMP/sec) is observed at varying filter fluxes in TFDF systems utilizing 1.5 mm or 2.0 mm TDF internal diameters. Significant increases in ΔTMP/sec are indicative of the formation of a gel layer on the inner surfaces of the tubular filtration elements (in this case TDFs) and signal fouling of the filter. The figure shows that, when operated at a fixed shear rate (γ) of 8000 s−1, the 1.5 mm TFDF setup exhibited fouling at fluxes above 400 L·m−2·hr−1, while the 2 mm TFDF setup exhibited no appreciable fouling at fluxes up to 2300 L·m−2·hr−1. Table 7, below, lists filter parameters and operating variables for both conditions; the systems differed principally in their respective TDF diameters and their Reynolds numbers at the feed, though different feed flow rates were used to achieve the same shear rate in both systems.

TABLE 7

Filter Parameters and Operating Variables For 1.5 And 2 mm TFDF Systems

| | 1.5 mm system | 2 mm system |
|---|---|---|
| TDF diameter (d) | 1.5 mm | 2.0 mm |
| Kinematic viscosity (μ) | 1.0 cSt | 1.0 cSt |
| TDF cross-sectional area (A) | 1.767 mm$^2$ | 3.142 mm$^2$ |
| Feed flow rate ($Q_F$) | $160 \frac{mL}{min}$ | $377 \frac{mL}{min}$ |
| Feed Velocity ($V_F$) | $1.509 \frac{m}{s}$ | $2 \frac{m}{s}$ |
| Shear Rate (γ) | 8048.131 s$^{-1}$ | 8000.188 s$^{-1}$ |
| Reynolds Number at feed ($Re_F$) | 2263.537 | 4000.094 |

CONCLUSION

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

Although embodiments of the present disclosure are described with specific reference to cultured mediums, including for use in bioprocessing, it should be appreciated that such systems and methods may be used in a variety of configurations of processing fluids, with a variety of instruments, and a variety of fluids.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. The term "or" is generally employed in its sense including "and/or" unless the content clearly dictates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

What is claimed is:

1. A bioprocessing system comprising:
   a process vessel;
   a tangential flow depth filtration (TFDF) unit comprising a thick-walled hollow fiber comprising a porous wall defining a lumen that is in fluid communication with the process vessel;
   a permeate fluid outlet in fluid communication with the porous wall; and wherein a density of the hollow fiber is between about 51% and about 56% of the density of an equivalent solid volume of the hollow fiber.

2. The bioprocessing system of claim 1, wherein an average pore size of the thick-walled hollow fiber is about 0.2 μm to about 10 μm.

3. The bioprocessing system of claim 1, wherein the density is about 53%.

4. The bioprocessing system of claim 1, wherein the porous wall has a thickness ranging from about 2 mm to about 7 mm.

5. The bioprocessing system of claim 1, wherein the thick-walled hollow fiber is formed from at least one polymer.

6. The bioprocessing system of claim 5, wherein the at least one polymer comprises polyethylene, polyethylene terephthalate, polybutylene terephthalate, nylon, polyvinylidene fluoride, polytetrafluoroethylene, or a combination thereof.

7. The bioprocessing system of claim 1, further comprising a polymer coating along an inside of the porous wall of the hollow fiber.

8. The bioprocessing system of claim 7, wherein the coating is selected from the group consisting of polyolefin, polyethylene, polypropylene, and polyvinylidene fluoride (PVDF).

9. The bioprocessing system of claim 7, wherein the coating on the porous wall reduces a pore size of the hollow fiber.

10. The bioprocessing system of claim 1, further comprising a polymer coating along an outside of the porous wall of the hollow fiber.

11. The bioprocessing system of claim 1, wherein the hollow fiber comprises bi-component filaments having a core and a coating.

12. The bioprocessing system of claim 11, wherein the bi-component filaments are further coated with polyvinylidene fluoride (PVDF).

13. A tangential flow depth filtration (TFDF) unit comprising:
a hollow fiber comprising a porous wall having a density between about 51% and about 56% of the density of an equivalent solid volume of the hollow fiber, the porous wall defining a lumen;
an inlet in fluid communication with the lumen; and
a permeate fluid outlet in fluid communication with the porous wall.

14. The TFDF unit of claim 13, further comprising a polymer coating along an inside of the porous wall of the hollow fiber.

15. The TFDF unit of claim 14, wherein the coating is selected from the group consisting of polyolefin and polyethylene.

16. The TFDF unit of claim 13, further comprising a polymer coating along an outside of the porous wall of the hollow fiber.

17. The TFDF unit of claim 13, wherein the hollow fiber comprises bi-component filaments having a core and a coating.

18. The TFDF unit of claim 13, wherein the thick-walled hollow fiber is formed from at least one polymer.

19. The TFDF unit of claim 18, wherein the at least one polymer comprises polyolefin, polypropylene, polyethylene, polyethylene terephthalate, polybutylene terephthalate, nylon, polyvinylidene fluoride, polytetrafluoroethylene, or a combination thereof.

20. A method of filtering a fluid, the method comprising:
flowing a fluid from a process vessel into a tangential flow depth filter (TFDF) unit comprising a thick-walled hollow fiber comprising a porous wall having a pore size and a density between about 51% and about 56% of the density of an equivalent solid volume of the hollow fiber, the porous wall defining a lumen that is in fluid communication with the process vessel, the TFDF unit having a permeate fluid outlet in fluid communication with the porous wall.

21. The method of claim 20, wherein the fluid is a culture medium comprising cells that have been cultured for a period of at least two days.

22. The method of claim 21, further comprising the step of adding a fluid volume to the process vessel equivalent to a volume of permeate, thereby maintaining an overall volume of the fluid.

23. The method of claim 20, wherein the permeate comprises a bioproduct produced by cells of the fluid.

24. The method of claim 20, the TFDF unit further comprising a polymer coating disposed along an inside of the porous wall of the hollow fiber.

25. The method of claim 24, wherein the coating is selected from the group consisting of polyolefin, polyethylene, and polypropylene polyvinylidene fluoride (PVDF).

26. The method of claim 20, the TFDF unit further comprising a polymer coating disposed along an outside of the porous wall of the hollow fiber.

27. The method of claim 20, wherein the hollow fiber comprises bi-component filaments having a core and a coating.

28. The method of claim 20, wherein the thick-walled hollow fiber is formed from at least one polymer.

29. The method of claim 28, wherein the at least one polymer comprises polyolefin, polypropylene, polyethylene, polyethylene terephthalate, polybutylene terephthalate, nylon, polyvinylidene fluoride, polytetrafluoroethylene, or a combination thereof.

* * * * *